(12) United States Patent
Greenberg et al.

(10) Patent No.: US 11,019,991 B2
(45) Date of Patent: *Jun. 1, 2021

(54) METHOD AND APPARATUS FOR FITTING A VISUAL PROSTHESIS USING ELECTRICALLY EVOKED RESPONSES

(71) Applicants: Second Sight Medical Products, Inc., Sylmar, CA (US); The Johns Hopkins University, Baltimore, MD (US)

(72) Inventors: Robert J Greenberg, Los Angeles, CA (US); Gislin Dagnelie, Baltimore, MD (US); Hendrik Christiaan Stronks, Gouda (NL)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/416,047

(22) Filed: May 17, 2019

(65) Prior Publication Data

US 2019/0269316 A1    Sep. 5, 2019

Related U.S. Application Data

(62) Division of application No. 13/311,264, filed on Dec. 5, 2011, now Pat. No. 10,292,579.

(60) Provisional application No. 61/419,663, filed on Dec. 3, 2010.

(51) Int. Cl.
*A61B 3/00* (2006.01)
*A61N 1/36* (2006.01)
*A61B 5/398* (2021.01)

(52) U.S. Cl.
CPC ............ *A61B 3/0025* (2013.01); *A61B 5/398* (2021.01); *A61N 1/36046* (2013.01)

(58) Field of Classification Search
CPC .. A61B 3/0025; A61B 5/0496; A61N 1/36046
See application file for complete search history.

(56) References Cited

U.S. PATENT DOCUMENTS

| | | | |
|---|---|---|---|
| 4,573,481 A | 3/1986 | Bullara | |
| 4,628,933 A | 12/1986 | Michelson | |
| 4,837,049 A | 6/1989 | Byers et al. | |
| 5,109,844 A | 5/1992 | de Juan, Jr. et al. | |

(Continued)

OTHER PUBLICATIONS

Walsh P, Kane N, Butler S. The clinical role of evoked potentials. Journal of Neurology, Neurosurgery & Psychiatry 2005;76:ii16-ii22.*

*Primary Examiner* — Christopher Koharski
*Assistant Examiner* — James Moss
(74) *Attorney, Agent, or Firm* — Scott Dunbar

(57) ABSTRACT

The invention is a method of automatically adjusting a visual prosthesis electrode array to the neural characteristics of an individual patient. By recording electrically evoked responses to a predetermined input stimulus, one can alter that input stimulus to the needs of an individual patient. A minimum input stimulus is applied to a patient, followed by recording an electrically evoked response to the input stimulus. By gradually increasing stimulus levels, one can determine the minimum input that creates a neural response, thereby identifying the threshold stimulation level. One can further determine a maximum level by increasing stimulus until a predetermined maximum neural response is obtained.

7 Claims, 18 Drawing Sheets

(56) References Cited

U.S. PATENT DOCUMENTS

| | | |
|---|---|---|
| 5,215,088 A | 6/1993 | Normann et al. |
| 5,935,155 A | 8/1999 | Humayun et al. |
| 6,208,894 B1 * | 3/2001 | Schulman .......... A61N 1/37252 |
| | | 607/2 |
| 6,400,989 B1 | 6/2002 | Eckmiller |
| 6,458,157 B1 | 10/2002 | Suaning |
| 6,547,746 B1 * | 4/2003 | Marino .................... A61B 5/04 |
| | | 600/544 |
| 7,483,751 B2 | 1/2009 | Greenberg et al. |
| 7,877,148 B2 | 1/2011 | Chowdhury et al. |
| 2006/0095108 A1 * | 5/2006 | Chowdhury ....... A61N 1/36046 |
| | | 607/141 |
| 2007/0273828 A1 | 2/2007 | Polland et al. |
| 2007/0093876 A1 * | 4/2007 | Greenberg .......... A61N 1/36046 |
| | | 607/53 |
| 2007/0188710 A1 * | 8/2007 | Hetling ................ A61B 5/0496 |
| | | 351/221 |
| 2007/0255343 A1 * | 11/2007 | McMahon ......... A61N 1/37247 |
| | | 607/54 |
| 2009/0219386 A1 | 3/2009 | Ebisawa |
| 2009/0091706 A1 | 4/2009 | Derr |
| 2009/0112287 A1 * | 4/2009 | Greenberg .......... G09B 21/008 |
| | | 607/54 |
| 2010/0014723 A1 * | 1/2010 | Addison ................ A61B 5/726 |
| | | 382/128 |
| 2010/0268302 A1 | 6/2010 | Botros |

\* cited by examiner

METHOD AND APPARATUS FOR FITTING A VISUAL PROSTHESIS USING ELECTRICALLY EVOKED RESPONSES

CROSS REFERENCE TO RELATED APPLICATIONS

This application is a divisional application of U.S. patent application Ser. No. 13/311,264, filed Dec. 5, 2011, to be issued as U.S. Pat. No. 10,292,579, for *Method and Apparatus for Fitting a Visual Prosthesis Using Electrically Evoked Electroretinograms*, which claims the benefit of U.S. provisional Patent Application Ser. No. 61/419,663, filed Dec. 3, 2010 for *Fitting a Visual Prosthesis using Electrically Evoked Electroretinograms*, the disclosure of which is incorporated herein by reference. This application is also related U.S. Pat. No. 7,483,751, *Automatic Fitting for a Visual Prosthesis*, the disclosure of which is incorporated by Reference.

FIELD

The present disclosure relates to visual prostheses configured to provide neural stimulation for the creation of artificial vision.

BACKGROUND

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular visual prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cats' retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Normann describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina and choroid/sclera, effectively pinning the retina against the choroid and the posterior aspects of the globe. Retinal tacks are one way to attach a retinal array to the retina. U.S. Pat. No. 5,109,844 to de Juan describes a flat electrode array placed against the retina for visual stimulation. U.S. Pat. No. 5,935,155 to Humayun describes a visual prosthesis for use with the flat retinal array described in de Juan.

A visual prosthesis must be adjusted to an individual patient. The most basic adjustment is mapping brightness levels to stimulation intensity, as this varies from patient to patient and from electrode to electrode for an individual patient. Hence, the visual prosthesis must be fit to the patient. As the number of active electrodes in a visual prosthesis increases, manually adjusting or fitting the visual prosthesis becomes tedious or impossible. Automatic fitting techniques are known such as those described in U.S. Pat. No. 7,483,751, Greenberg et al, *Automatic Fitting for a Visual Prosthesis*. Greenberg describes automatic fitting using iris sphincter response, retinal recordings and cortical recordings. These techniques are effective but very expensive to implement.

SUMMARY

The invention is a method of automatically adjusting a retinal electrode array to the neural characteristics of an individual patient. By recording electrically evoked electroretinogram (eERG) responses to a predetermined input stimulus, one can alter that input stimulus to the needs of an individual patient. A minimum input stimulus is applied to a patient, while simultaneously recording an eERG containing the response to the input stimulus. By repeating stimulation and recording at gradually increasing stimulus levels, one can determine the minimum input that creates a neural response, thereby identifying the threshold stimulation level. One can further determine a maximum level by increasing stimulus until a predetermined maximum neural response is obtained. However, eERG signals include a significant amount of noise. Applicants have developed novel techniques for artifact reduction and noise filtering to provide an accurate measure of neural activity.

According to a first aspect of the invention, a method of fitting a visual prosthesis is proposed, including stimulating visual neurons with an electrical signal, detecting an indication of neural activity using an electroretinogram, comparing the indication of neural activity to a desired level of neural activity, and altering the electrical signal based upon a comparison of the indication of neural activity and the desired level of neural activity.

According to a second aspect of the invention, the method according to aspect one, further includes applying a wavelet transform to the indication of neural activity According to a third aspect of the invention, the method further includes detecting an indication of neural activity in the fellow eye using an electroretinogram and subtracting the indication of neural activity in the fellow eye from the indication of neural activity in the implanted eye.

According to a fourth aspect of the invention, the method according to aspect one, wherein the step of stimulating visual neurons includes increasing the electrical charge until an indication of neural activity is detected.

Further embodiments are shown in the specification, drawings and claims of the present application.

BRIEF DESCRIPTION OF THE FIGURES

FIGS. 14-1, 14-2, 14-3 and 14-4 show an exemplary embodiment of a video processing unit. FIG. 14-1 should be viewed at the left of FIG. 14-2. FIG. 14-3 should be viewed at the left of FIG. 14-4. FIGS. 14-1 and 14-2 should be viewed on top of FIGS. 14-3 and 14-4.

Figure 1:
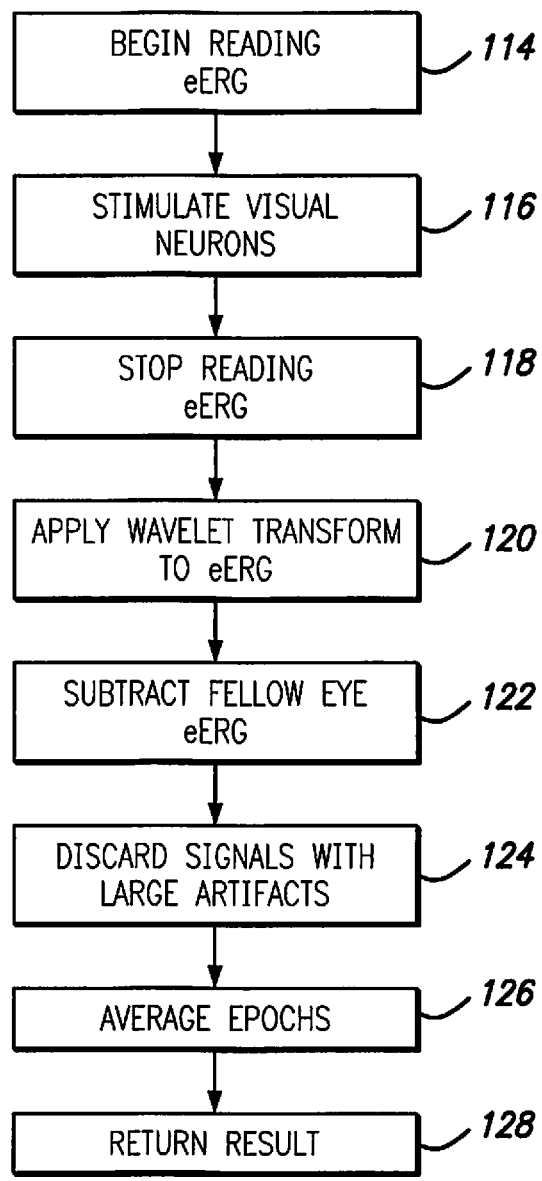
FIG. 1 is a flow chart showing the method of processing eERG signals.

In the following description, like reference numbers are used to identify like elements. Furthermore, the drawings are intended to illustrate major features of exemplary embodiments in a diagrammatic manner. The drawings are not intended to depict every feature of every implementation nor relative dimensions of the depicted elements, and are not drawn to scale.

DETAILED DESCRIPTION

The present disclosure is concerned with a visual apparatus and a method for creation of artificial vision. In particular, the present disclosure provides a means of automatically fitting a visual prosthesis using an eERG.

Subjects implanted with an *Argus*® II retinal prosthesis in the right eye (OD) participated in a study. Binocular eERGs were obtained, using Burian-Allen contact lens electrodes, by averaging up to 2750 epochs. Current levels ranged from below perceptual threshold to a maximum of ~50 µA per electrode. Signal-to-noise ratios of raw eERGs were increased off-line using wavelet transformation (WT), for example the symlet 5 transform. The eERG was expected to be measurable only in OD. Eye movements and pupil responses may contribute to the eERG, but will also evoke a response in the contralateral or fellow eye (OS), since they are centrally controlled. Therefore, pupil and eye movements were recorded with an eye tracker, averaging up to 30 responses;

eERG responses were recorded, which consisted of a negative peak ($N_1$) followed by a positive peak ($P_1$). In most subjects eERGs can be obtained bilaterally. We performed eye tracking and eERG recordings before and after eye dilation with tropicamide (1%) and phenylephrin (2.5%). At 30 µA, the pupil dilated in both eyes at 0.6 s, followed by a bilateral constriction after 1.2 s, with smaller amplitudes in the implanted than in the fellow eye (−0.1, +0.3 vs. −0.2, +0.5 mm). Pharmacologic dilation abolished these pupil responses. Eye movements were small (0.1 mm or less). Before dilation, the eERG $N_1$-$P_1$ amplitude was 6 µV in both eyes. After dilation, the eERG amplitude was 2 µV in both eyes. To remove bilateral electrically evoked artifacts we subtracted the OS eERG from the OD eERG. No dilation drops were applied. Using this subtraction procedure we obtained reliable eERGs. At current levels between perceptual threshold and maximum comfort level, eERG amplitudes were 2-5 µV, $N_1$ latencies were 100-200 ms, and $P_1$ latencies 300-400 ms. eERG amplitudes correlated significantly (F-test, $P<0.05$, $r^2>0.9$) with stimulus level.

Bilateral artifacts, such as pupil responses, in the corneal eERG cannot be sufficiently reduced by using dilation drops. Even after dilation, a residual, but substantial electrical response persisted in the contralateral eye. This residual activity might reflect the neural component of the pupil reflex, while the myogenic component is blocked after dilation. Subtracting the contralateral eERG yields the best approximation of the eERG.

FIG. 1 shows the filtering process applied to the eERG signal according to the present invention. Simultaneously, eERG signals are recorded in the stimulated eye and the fellow eye 114. Visual neurons are stimulated using the visual prosthesis 116. eERG recording stops 118. Temporal alignment of the two eERG signals and the stimulus is important to remove the unwanted signal components. Next, a stationary wavelet transform, for example a symlet 5 transform, is applied to the eERG signal from both eyes to filter out any artifact caused by the implanted electronics 120. Particularly, the telemetry coils of the visual prosthesis generate substantial noise. Next, the eERG signal from the fellow eye is subtracted from the eERG signal from the stimulated eye 122 to reduce biological artifacts, such as those associated with eye movement and pupil responses. Since, both eyes move together and both pupils respond together, subtracting the signal from the fellow eye removes the eye movement and pupil response artifacts. Next, eERG waveforms with a peak-to-peak amplitude exceeding a predetermined level in the first second are discarded 124. This eliminates those responses with large artifacts that are not bilaterally symmetrical. The predetermined level is between 40 µV and 60 µV, but preferably 50 µV. Last, 100 to 200 epochs are averaged 126 to reduce random noise, such as background noise and small eye movements. Finally, the output is returned and used the fitting process as described with respect to FIG. 2 in step 128 of FIG. 1.

Figure 2:
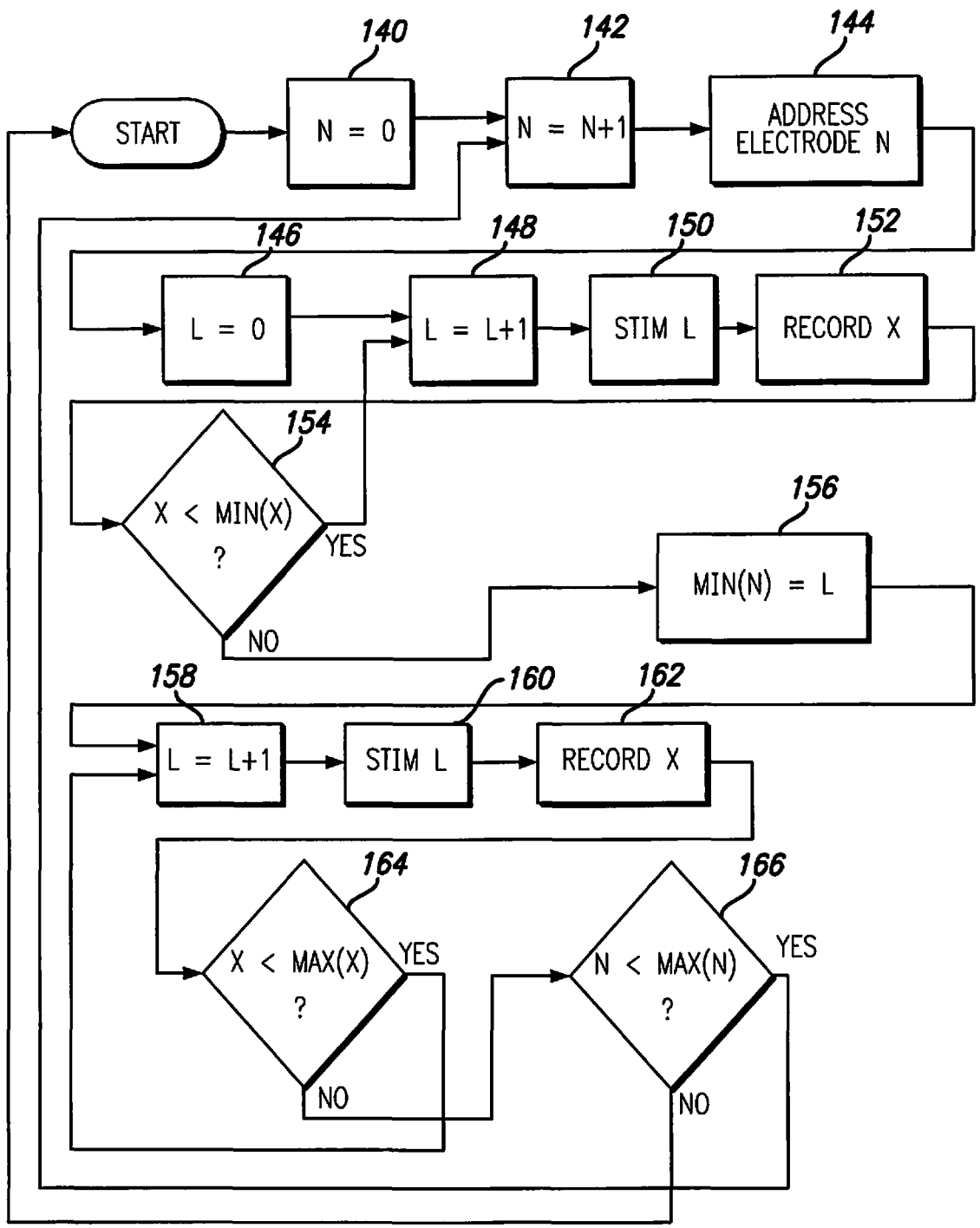
FIG. 2 is a flow chart showing the process of auto fitting an electrode array.

FIG. 2 is a flow chart of the automatic fitting sequence. In the flow chart, the value N is the initial selected electrode, X is the neural activity recorded, and L is the level of stimulation. First L is set to 0, or some level known to be below the threshold of perception 140 and then incremented 142. Electrode N is addressed 144. The stimulation level is set to zero 146, and then incremented 148. The neural tissue is stimulated at the minimum level 150. The stimulation is immediately followed by a recording of activity in the eERG 152. One must be careful to distinguish between neural activity and electrical charge from the stimulating electrode. The neural response follows stimulation (see FIG. 4). Simultaneous stimulation and recording requires that the recording phase be longer than the stimulation phase. If so, the stimulation and neural response can be separated digitally. If the recorded neural activity is less than a predetermined level 154, the stimulation level is increased and steps 148-154 are repeated. While this is preferably a fully automatic process, it may be advantageous to first fit a subset of the electrodes using patient responses to properly calibrate the desired eERG signal levels.

Once minimum neural activity is recorded, the stimulation level is saved in memory 156. The level is then further increased 158 and stimulation is repeated 160. Again stimulation is immediately followed by recording neural activity 162. If a predetermined maximum level has not been reached, steps 158-164 are repeated until the predetermined maximum stimulation level is obtained. Once the predetermined maximum stimulation level is obtained, steps 142-164 are repeated for the next electrode. The process is continued until a minimum and maximum stimulation level is determined for each electrode 166.

The maximum stimulation level borders on discomfort for the patient. Because the automatic fitting process is automated, high levels of stimulation are only applied for a few microseconds. This significantly decreases the level of discomfort for the patient compared with stimulating long enough to elicit a response from the patient.

The fitting process is described above as an incremental process. The fitting process may be expedited by more efficient patterns. For example changes may be made in large steps if it the detected response is significantly below the desired response, followed by increasingly small steps as the desired response draws near. The system can jump above and below the desired response dividing the change by half with each step.

Often, neural response in a retina is based, in part, geographically. That is, neurons closer to the fovea require less stimulation than neurons farther from the fovea. Stimulation levels are also higher when the electrodes array does not contact the retina. Hence once a stimulation is level is set for an electrode, one can presume that the level will be similar for an adjacent electrode. The fitting process may be expedited by starting at a level near the level set for a previously fit adjacent electrode.

Automating the fitting process has many advantages. It greatly expedites the process reducing the efforts of the patient and clinician. Further, the automated process is objective. Patient responses are subjective and may change over time due to fatigue. In some cases, a patient may not be able to provide the required responses due to age, disposition, and/or limited metal ability.

Figure 3:
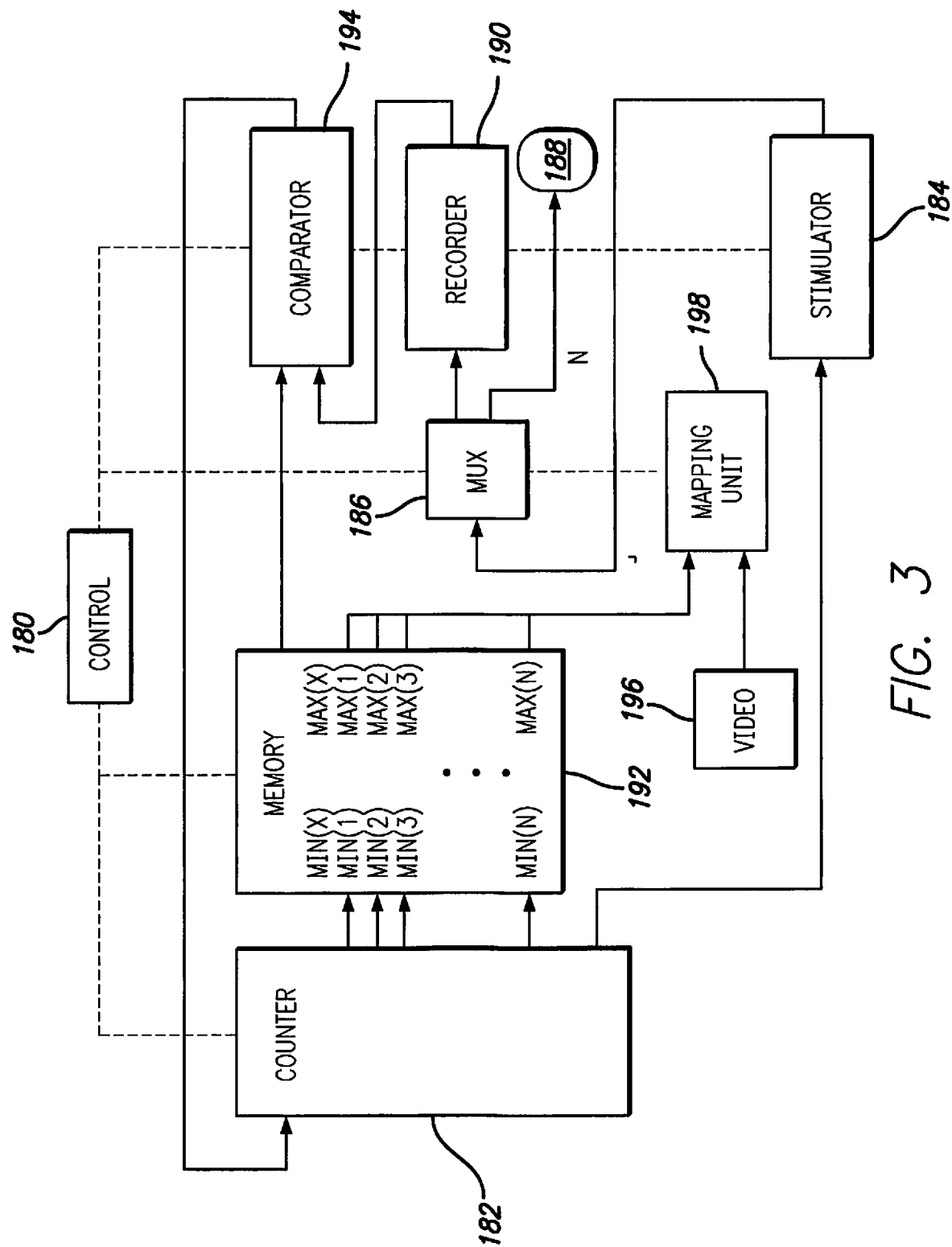
FIG. 3 depicts a block diagram of the visual prosthesis electronic control unit.

FIG. 3 depicts a block diagram of the control unit. The block diagram is a functional diagram. Many of the functional units would be implemented in a microprocessor. A control unit 180 sets and increments a counter 182 to control the stimulation level of the stimulator 184. The stimulation signal is multiplexed in MUX 186 to address individual electrodes 188. After each stimulation step, the eERG returns a neural activity signal to a recorder 190. The signal is compared to the stored minimum or maximum level (stored in a memory 192) in a comparator 194. After programming, a signal from a video source 196, or other neural stimulation source, is adjusted in a mapping unit 198, in accordance with the minimum and maximum levels stored in the memory 192. The adjusted signal is sent to the stimulator 184, which in synchronization with MUX 186 applies the signal to the electrodes 188. The electronics for the control unit could be external or within the implanted prosthesis.

Figure 4:
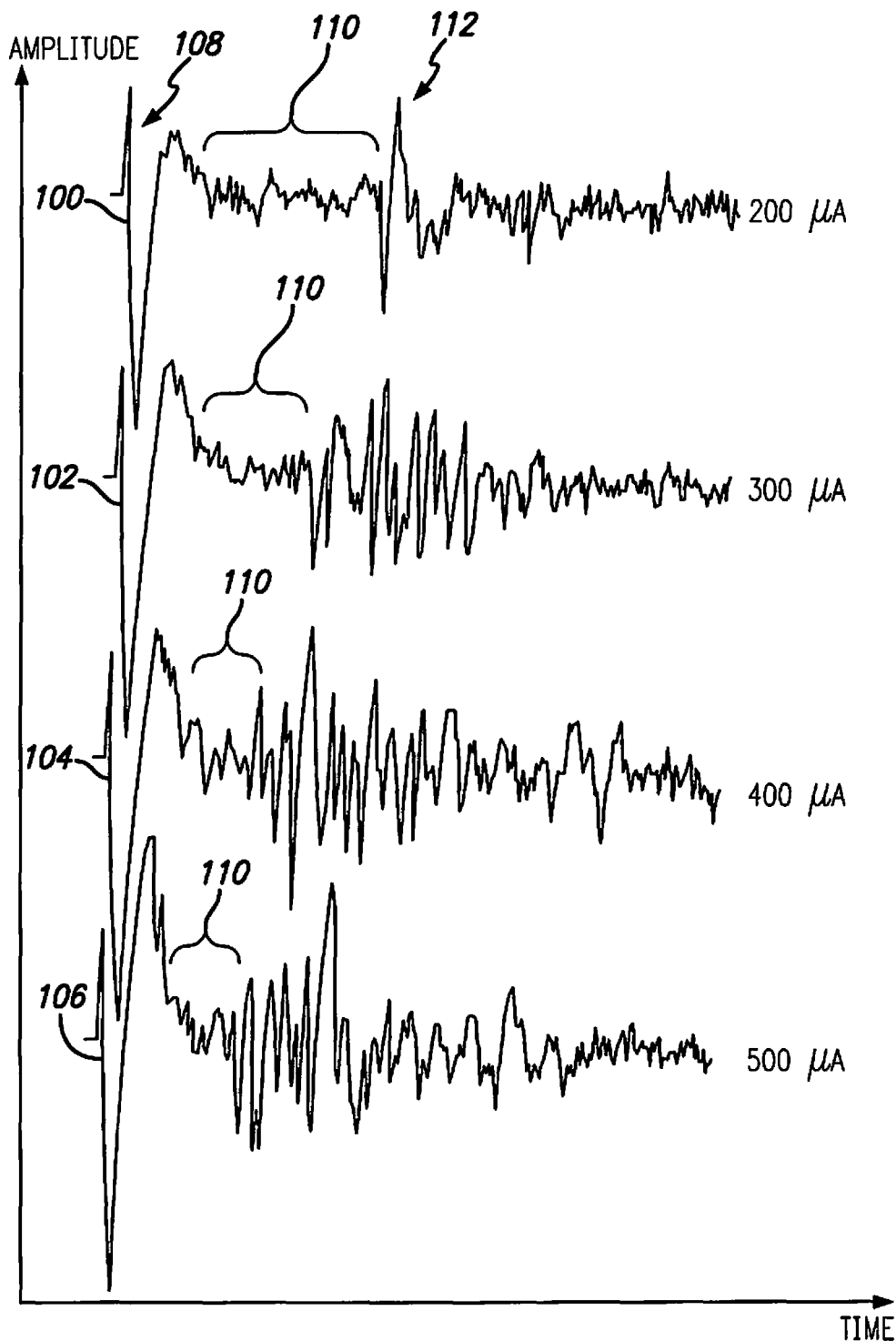
FIG. 4 is a graph depicting a typical neural response to electrical input.

FIG. 4 is a graphical representation of the neural response to electrical stimulus. The vertical axis is current while the horizontal axis is time. Four curves 100-106 show the response at varying input current levels. An input pulse 108, is followed by a brief delay 110, and a neural response 112. Hence, it is important to properly time the detecting function. It should also be noted that the delay period 110 becomes shorter with increased stimulation current. Hence, the system must separate the stimulation signals and neural response faster with increased current. The change in delay time may also be used as an additional indication of neural response. That is, the minimum and maximum may be determined by matching predetermined delay times rather than predetermined output levels.

Figure 5:
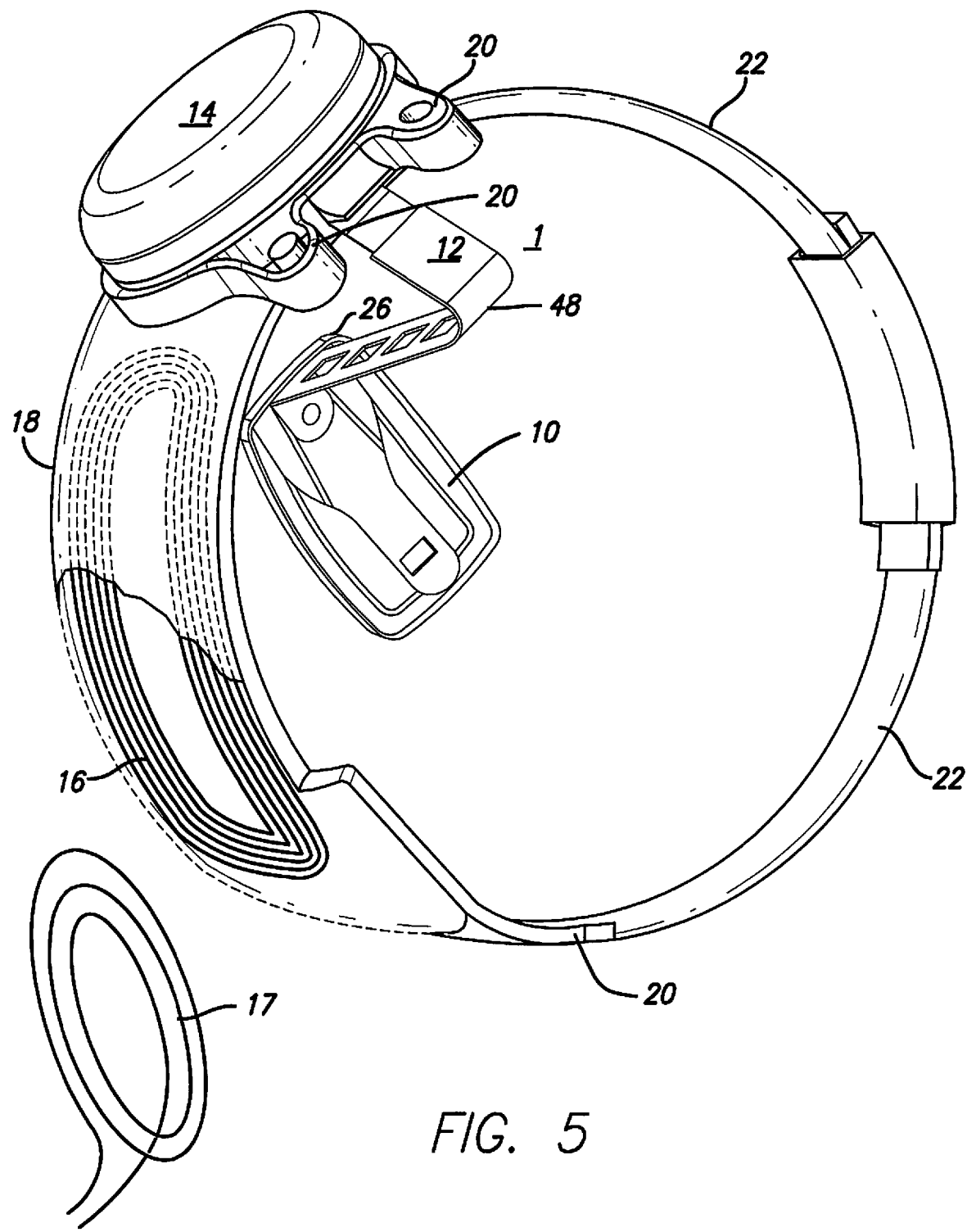
FIGS. 5 and 6 show a retinal stimulation system adapted to be implanted into a subject.
Figure 6:
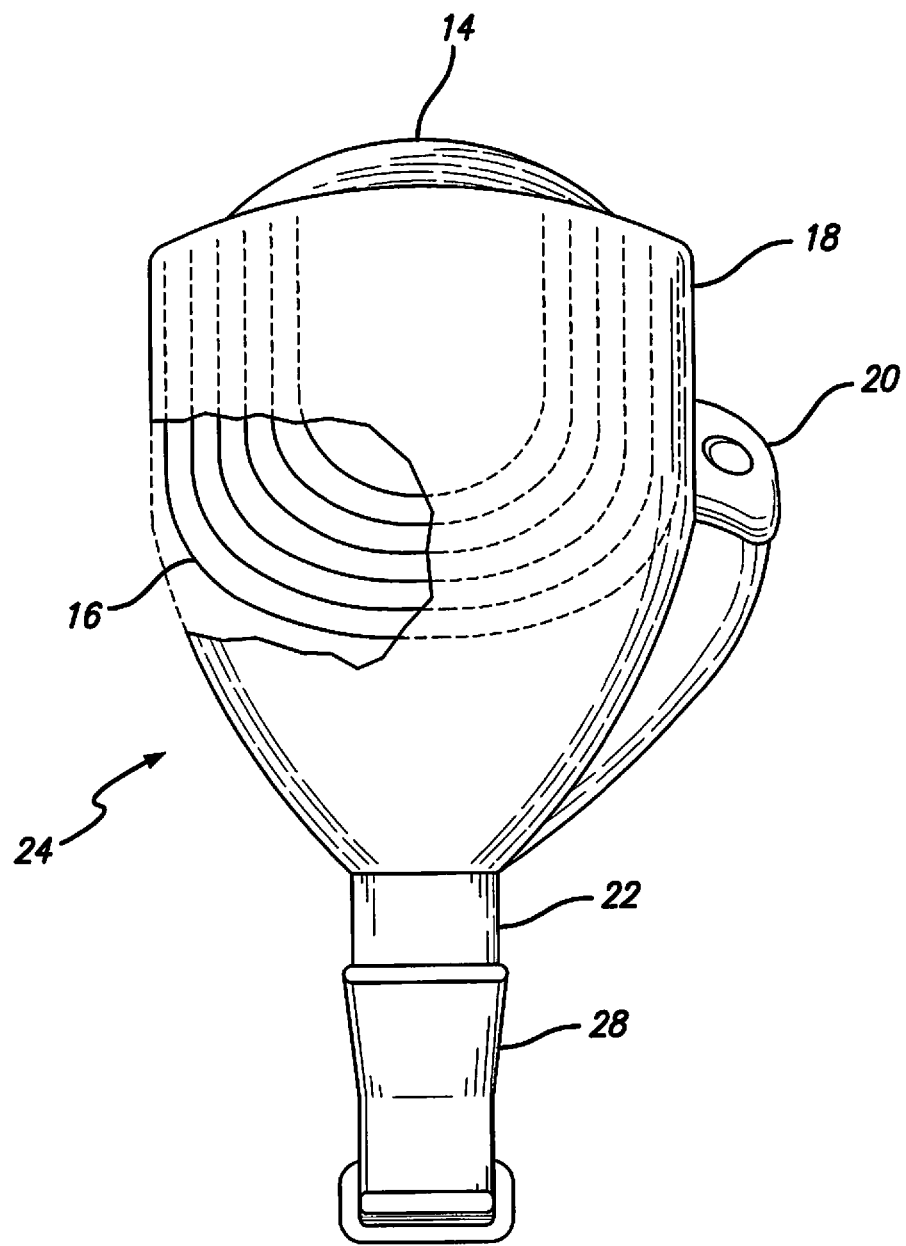

The exemplary retinal stimulation system shown in FIGS. 5 and 6, is an implantable electronic device containing an inductive coil 16 and an electrode array 10 that is electrically coupled by a cable 48 that pierces sclera of the subject's eye to an electronics package 14, external to the sclera. The retinal stimulation system is designed, for example, to elicit visual percepts in blind subjects with retinitis pigmentosa.

Human vision provides a field of view that is wider than it is high. This is partially due to fact that we have two eyes, but even a single eye provides a field of view that is approximately 90° high and 140° to 160° degrees wide. It is therefore, advantageous to provide a flexible circuit electrode array 10 that is wider than it is tall. This is equally applicable to a cortical visual array. In which case, the wider dimension is not horizontal on the visual cortex, but corresponds to horizontal in the visual scene.

FIGS. 5 and 6 present the general structure of a visual prosthesis used in implementing the invention.

FIG. 5 shows a perspective view of the implanted portion of the preferred retinal prosthesis. A flexible circuit 1 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The secondary inductive coil receives power and data from a primary inductive coil 17, which is external to the body. The electronics package 14 and secondary inductive coil 16 are held together by the molded body 18. The molded body 18 holds the electronics package 14 and secondary inductive coil 16 end to end. The molded body 18 holds the secondary inductive coil 16 and electronics package 14 in the end to end orientation and minimizes the thickness or height above the sclera of the entire device. The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil. It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.\

FIG. 6 shows a side view of the implanted portion of the retinal prosthesis, in particular, emphasizing the fan tail 24. When implanting the retinal prosthesis, it is necessary to pass the strap 22 under the eye muscles to surround the sclera. The secondary inductive coil 16 and molded body 18 must also follow the strap 22 under the lateral rectus muscle on the side of the sclera. The implanted portion of the retinal prosthesis is very delicate. It is easy to tear the molded body 18 or break wires in the secondary inductive coil 16. In order to allow the molded body 18 to slide smoothly under the lateral rectus muscle, the molded body 18 is shaped in the form of a fan tail 24 on the end opposite the electronics package 14. The strap 22 further includes a hook 28 the aids the surgeon in passing the strap under the rectus muscles.

Figure 7:
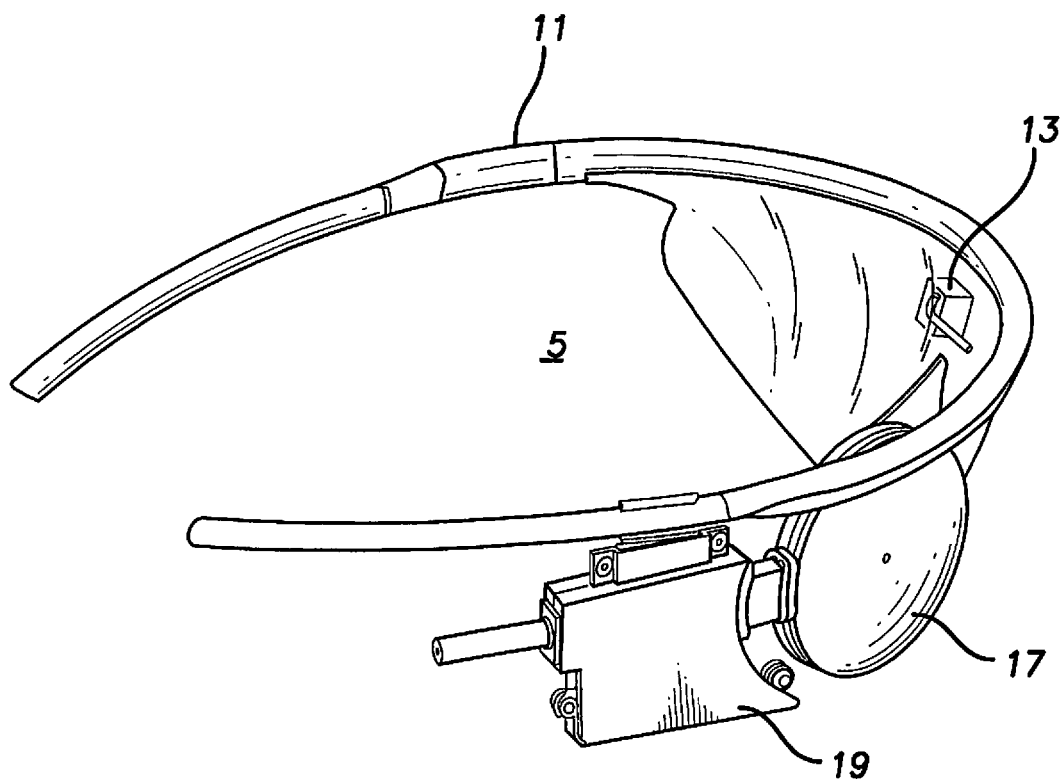
FIGS. 7 and 8 show a video capture/transmission apparatus or visor adapted to be used in combination with the retinal stimulation of FIGS. 5 and 6.
Figure 8:
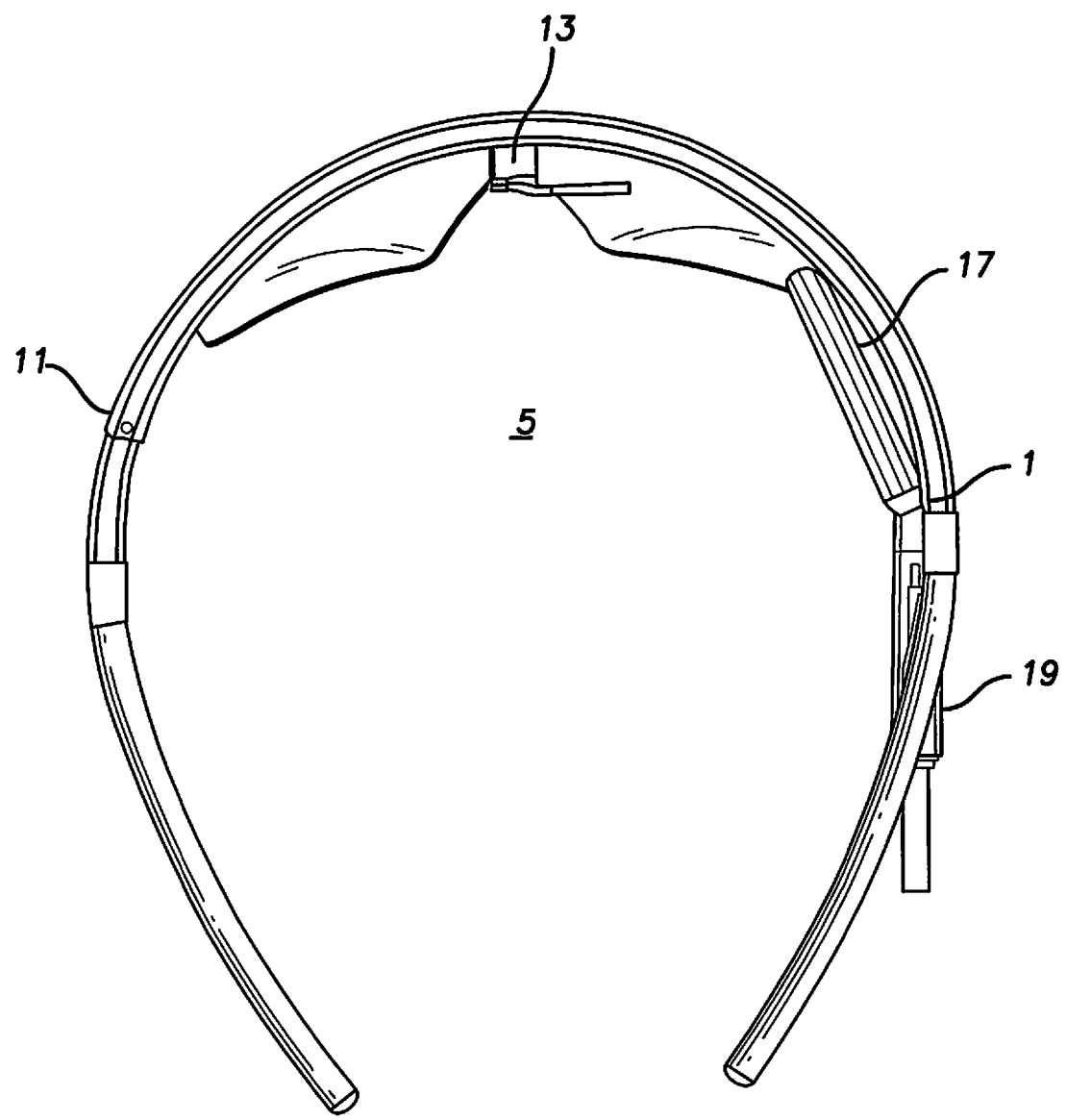

Referring to FIGS. 7 and 8, the glasses 5 may comprise, for example, a frame 11 holding a camera 13, an external coil 17 and a mounting system 19 for the external coil 17. The mounting system 19 may also enclose the RF circuitry. In this configuration, the video camera 13 captures live video. The video signal is sent to an external Video Processing Unit (VPU) 20 (shown in FIGS. 9, 11 and 12 and discussed below), which processes the video signal and subsequently transforms the processed video signal into electrical stimulation patterns or data. The electrical stimulation data are then sent to the external coil 17 that sends both data and power via radio-frequency (RF) telemetry to the coil 16 of the retinal stimulation system, shown in FIGS. 5 and 6. The coil 16 receives the RF commands which control an application specific integrated circuit (ASIC) which in turn delivers stimulation to the retina of the subject via a thin film electrode array (TFEA). In one aspect of an embodiment, light amplitude is recorded by the camera 13. The VPU 20 may use a logarithmic encoding scheme to convert the incoming light amplitudes into the electrical stimulation patterns or data. These electrical stimulation patterns or data may then be passed on to the Retinal Stimulation System, which results in the retinal cells being stimulated via the electrodes in the electrode array 10 (shown in FIGS. 5 and 6). In one exemplary embodiment, the electrical stimulation patterns or data being transmitted by the external coil 17 is binary data. The external coil 17 may contain a receiver and transmitter antennae and a radio-frequency (RF) electronics card for communicating with the internal coil 16.

Figure 9:
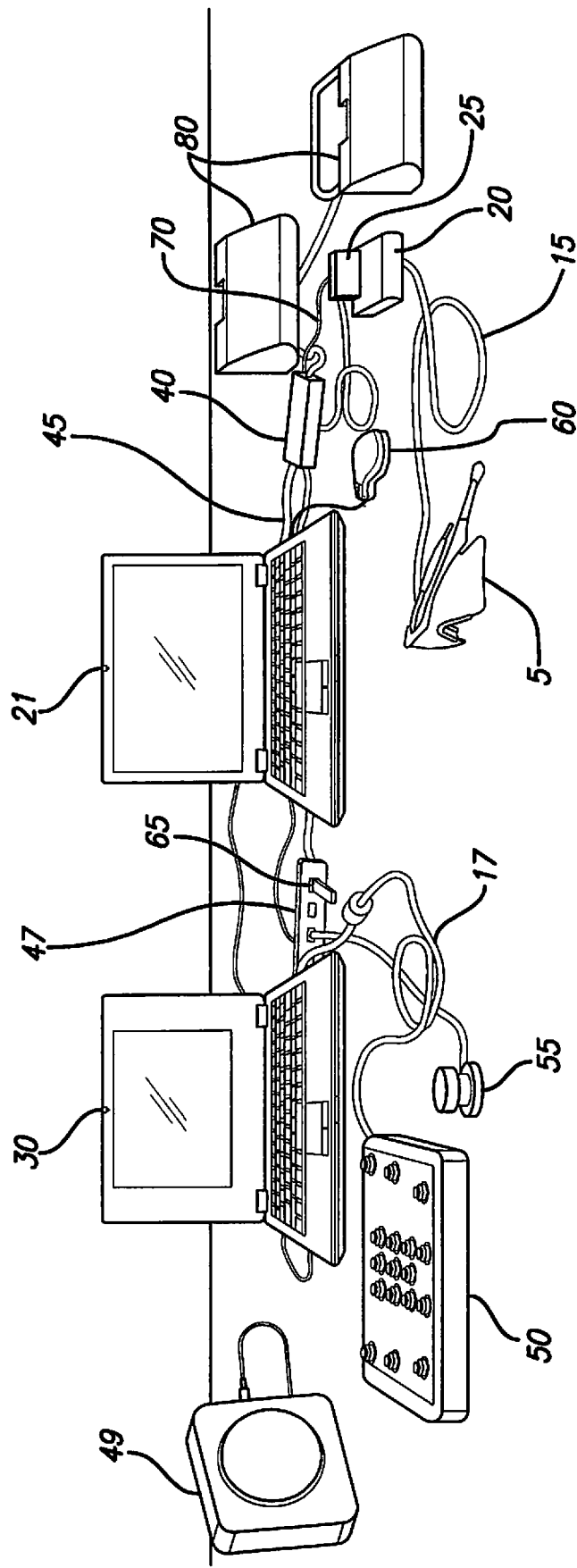
FIG. 9 shows components of a fitting system according to the present disclosure, the system also comprising the visor shown in FIGS. 4 and 5.

Referring to FIG. 9, a Fitting System (FS) may be used to configure and optimize the visual prosthesis apparatus. The Fitting System is fully described in the related application U.S. application Ser. No. 11/796,425, filed on Apr. 27, 2007, which is incorporated herein by reference in its entirety.

The Fitting System may comprise custom software with a graphical user interface running on a dedicated laptop computer 21. Within the Fitting System are modules for performing diagnostic checks of the implant, loading and executing video configuration files, viewing electrode voltage waveforms, and aiding in conducting psychophysical experiments. A video module can be used to download a video configuration file to the Video Processing Unit (VPU) 20 discussed above and store it in non-volatile memory to control various aspects of video configuration, e.g. the spatial relationship between the video input and the electrodes. The software can also load a previously used video configuration file from the VPU 20 for adjustment.

The Fitting System can be connected to the Psychophysical Test System (PTS), located for example on a dedicated laptop 30, in order to run psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB® (MathWorks®) software and other tools to allow the clinicians to develop customized psychophysics experiment scripts.

Using the psychophysics module, important perceptual parameters such as perceptual threshold, maximum comfort level, and spatial location of percepts may be reliably measured. Based on these perceptual parameters, the fitting software enables custom configuration of the transformation between video image and spatio-temporal electrode stimulation parameters in an effort to optimize the effectiveness of the retinal prosthesis for each subject.

The Fitting System laptop 21 of FIG. 9 may be connected to the VPU 20 using an optically isolated serial connection adapter 40. Because it is optically isolated, the serial connection adapter 40 assures that no electric leakage current can flow from the Fitting System laptop 10 in the event of a fault condition.

As shown in FIG. 9, the following components may be used with the Fitting System according to the present disclosure. The Video Processing Unit (VPU) 20 for the subject being tested, a Charged Battery 25 for VPU 20, the Glasses 5, a Fitting System (FS) Laptop 10, a Psychophysical Test System (PTS) Laptop 30, a PTS CD (not shown), a Communication Adapter (CA) 40, a USB Drive (Security) (not shown), a USB Drive (Transfer) 47, a USB Drive (Video Settings) (not shown), a Patient Input Device (RF Tablet) 50, a further Patient Input Device (Jog Dial) 55, Glasses Cable 15, CA-VPU Cable 70, FS-CA Cable 45, FS-PTS Cable 46, Four (4) Port USB Hub 47, Mouse 60, Test Array system 80, Archival USB Drive 49, an Isolation Transformer (not shown), adapter cables (not shown), and an External Monitor (not shown).

With continued reference to FIG. 9, the external components of the Fitting System may be configured as follows. The battery 25 is connected with the VPU 20. The PTS Laptop 30 is connected to FS Laptop 10 using the FS-PTS Cable 46. The PTS Laptop 30 and FS Laptop 10 are plugged into the Isolation Transformer (not shown) using the Adapter Cables (not shown). The Isolation Transformer is plugged into the wall outlet. The four (4) Port USB Hub 47 is connected to the FS laptop 10 at the USB port. The mouse 60 and the two Patient Input Devices 50 and 55 are connected to four (4) Port USB Hubs 47. The FS laptop 10 is connected to the Communication Adapter (CA) 40 using the FS-CA Cable 45. The CA 40 is connected to the VPU 20 using the CA-VPU Cable 70. The Glasses 5 are connected to the VPU 20 using the Glasses Cable 15.

In one exemplary embodiment, the Fitting System shown in FIG. 9 may be used to configure system stimulation parameters and video processing strategies for each subject outfitted with the visual prosthesis apparatus. The fitting application, operating system, laptops 21 and 30, isolation unit and VPU 20 may be tested and configuration controlled as a system. The software provides modules for electrode control, allowing an interactive construction of test stimuli with control over amplitude, pulse width, and frequency of the stimulation waveform of each electrode in the Retinal stimulation system. These parameters are checked to ensure that maximum charge per phase limits, charge balance, and power limitations are met before the test stimuli are presented to the subject. Additionally, these parameters may be checked a second time by the VPU 20's firmware. The Fitting System shown in FIG. 9 may also provide a psychophysics module for administering a series of previously determined test stimuli to record subject's responses. These responses may be indicated by a keypad 50 and/or verbally. The psychophysics module may also be used to reliably measure perceptual parameters such as perceptual threshold, maximum comfort level, and spatial location of percepts. These perceptual parameters may be used to custom configure the transformation between the video image and spatio-temporal electrode stimulation parameters thereby optimizing the effectiveness of the visual prosthesis for each subject. The Fitting System is fully described in the related application U.S. application Ser. No. 11/796,425, filed on Apr. 27, 2007, which is incorporated herein by reference in its entirety.

The visual prosthesis apparatus may operate in two modes: i) stand-alone mode and ii) communication mode.

Stand-Alone Mode

Figure 10:
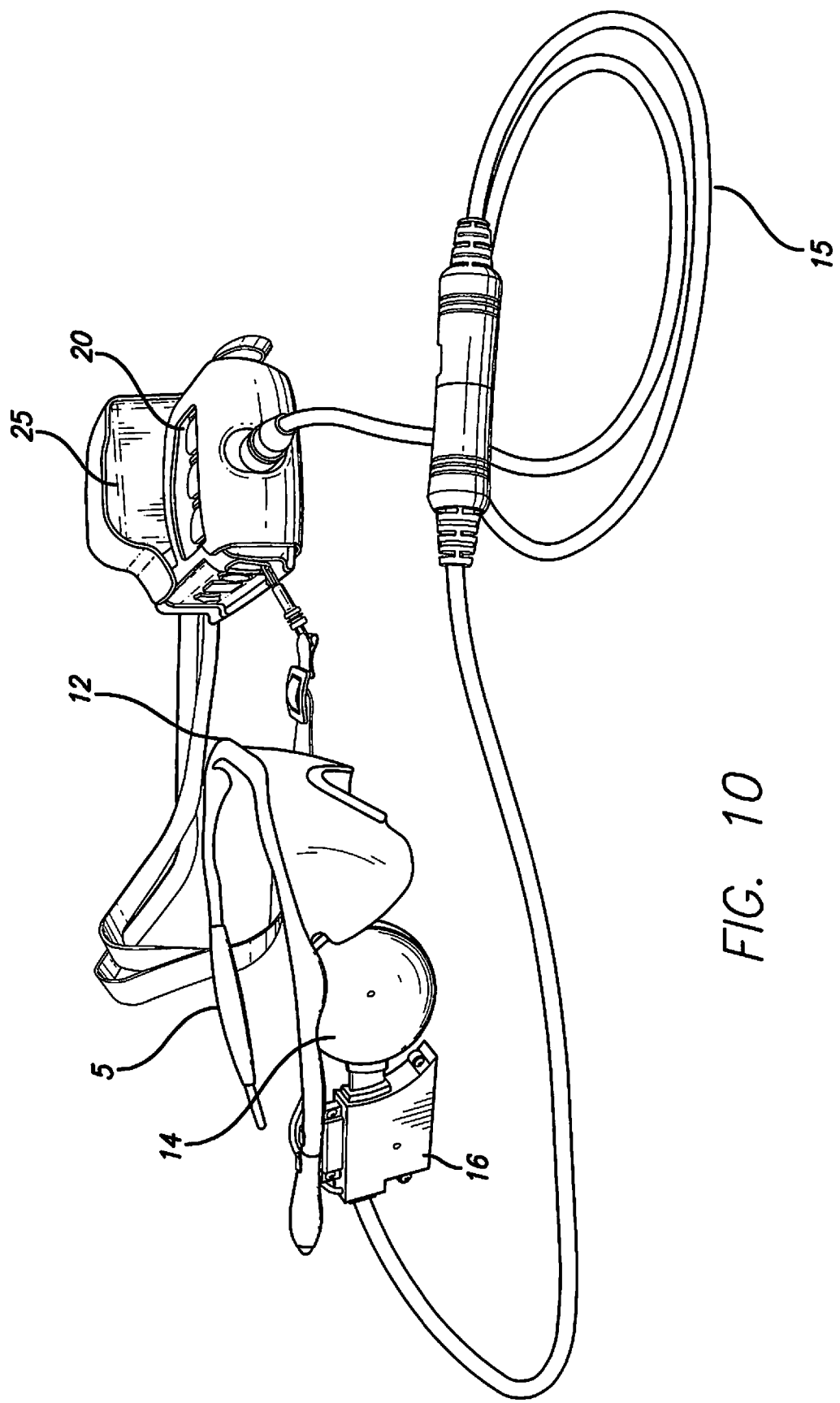
FIG. 10 shows the visual prosthesis apparatus in a stand-alone mode, i.e. comprising the visor connected to a video processing unit.

Referring to FIG. 10, in the stand-alone mode, the video camera 13, on the glasses 5, captures a video image that is sent to the VPU 20. The VPU 20 processes the image from the camera 13 and transforms it into electrical stimulation patterns that are transmitted to the external coil 17. The external coil 17 sends the electrical stimulation patterns and power via radio-frequency (RF) telemetry to the implanted retinal stimulation system. The internal coil 16 of the retinal stimulation system receives the RF commands from the external coil 17 and transmits them to the electronics package 14 that in turn delivers stimulation to the retina via the electrode array 10. Additionally, the retinal stimulation system may communicate safety and operational status back to the VPU 20 by transmitting RF telemetry from the internal coil 16 to the external coil 17. The visual prosthesis apparatus may be configured to electrically activate the retinal stimulation system only when it is powered by the VPU 20 through the external coil 17. The stand-alone mode may be used for clinical testing and/or at-home use by the subject.

Communication Mode

The communication mode may be used for diagnostic testing, psychophysical testing, patient fitting and downloading of stimulation settings to the VPU 20 before transmitting data from the VPU 20 to the retinal stimulation system as is done for example in the stand-alone mode described above. Referring to FIG. 9, in the communication mode, the VPU 20 is connected to the Fitting System laptop 21 using cables 70, 45 and the optically isolated serial connection adapter 40. In this mode, laptop 21 generated stimuli may be presented to the subject and programming parameters may be adjusted and downloaded to the VPU 20. The Psychophysical Test System (PTS) laptop 30 connected to the Fitting System laptop 21 may also be utilized to perform more sophisticated testing and analysis as fully described in the related application U.S. application Ser. No. 11/796,425, filed on Apr. 27, 2007, which is incorporated herein by reference in its entirety.

In one embodiment, the functionality of the retinal stimulation system can also be tested pre-operatively and intra-operatively (i.e. before operation and during operation) by using an external coil 17, without the glasses 5, placed in close proximity to the retinal stimulation system. The coil 17 may communicate the status of the retinal stimulation system to the VPU 20 that is connected to the Fitting System laptop 21 as shown in FIG. 9.

As discussed above, the VPU 20 processes the image from the camera 13 and transforms the image into electrical stimulation patterns for the retinal stimulation system. Filters such as edge detection filters may be applied to the electrical stimulation patterns for example by the VPU 20 to generate, for example, a stimulation pattern based on filtered video data that the VPU 20 turns into stimulation data for the retinal stimulation system. The images may then be reduced in resolution using a downscaling filter. In one exemplary embodiment, the resolution of the image may be reduced to match the number of electrodes in the electrode array 10 of the retinal stimulation system. That is, if the electrode array has, for example, sixty electrodes, the image may be reduced to a sixty channel resolution. After the reduction in resolution, the image is mapped to stimulation intensity using for example a look-up table that has been derived from testing of individual subjects. Then, the VPU 20 transmits the stimulation parameters via forward telemetry to the retinal stimulation system in frames that may employ a cyclic redundancy check (CRC) error detection scheme.

Figure 11:
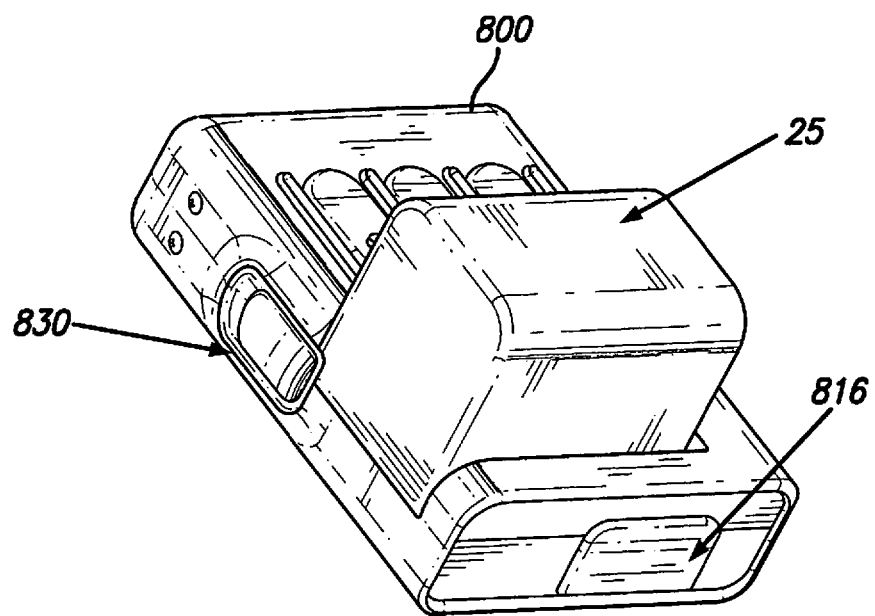
FIGS. 11-12 show the video processing unit already briefly shown with reference to FIG. 9.
Figure 12:
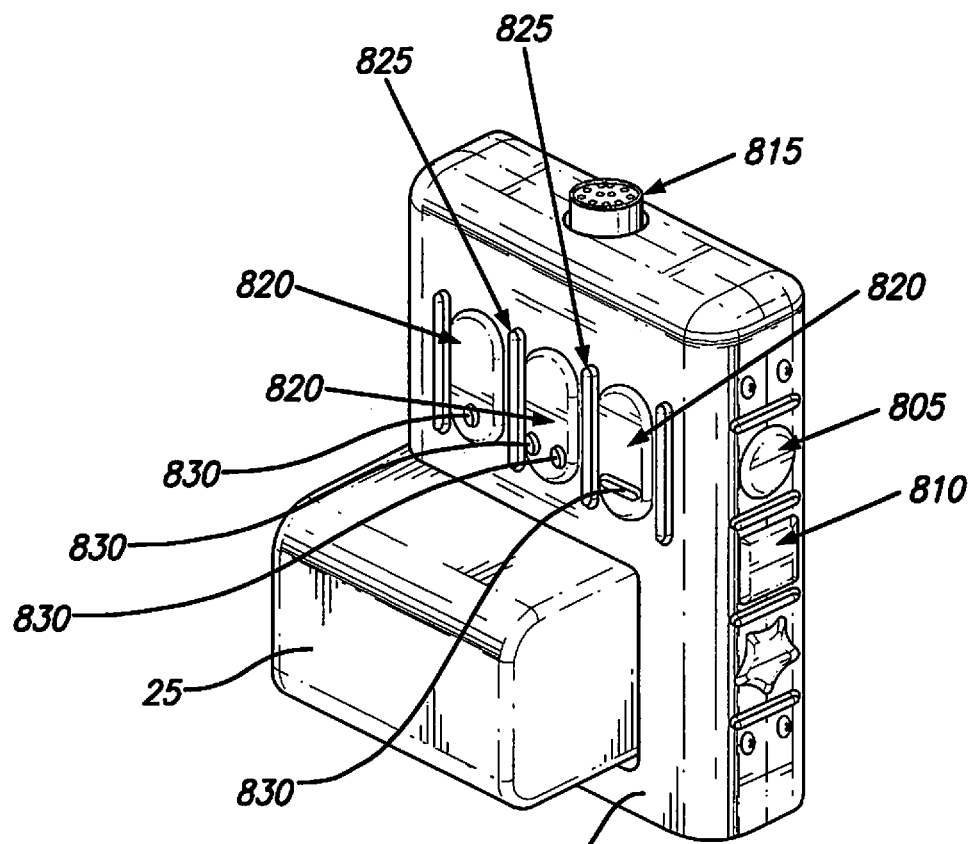

In one exemplary embodiment, the VPU 20 may be configured to allow the subject/patient i) to turn the visual prosthesis apparatus on and off, ii) to manually adjust settings, and iii) to provide power and data to the retinal stimulation system. Referring to FIGS. 11 and 12, the VPU 20 may comprise a case 800, power button 805 for turning the VPU 20 on and off, setting button 810, zoom buttons 820 for controlling the camera 13, connector port 815 for connecting to the Glasses 5, a connector port 816 for connecting to the laptop 21 through the connection adapter 40, indicator lights 825 to give visual indication of operating status of the system, the rechargeable battery 25 for powering the VPU 20, battery latch 830 for locking the battery 25 in the case 800, digital circuit boards (not shown), and a speaker (not shown) to provide audible alerts to indicate various operational conditions of the system. Because the VPU 20 is used and operated by a person with minimal or no vision, the buttons on the VPU 20 may be differently shaped and/or have special markings as shown in FIG. 12 to help the user identify the functionality of the button without having to look at it. As shown in FIG. 12, the power button 805 may be a circular shape while the settings button 820 may be square shape and the zoom buttons 820 may have special raised markings 830 to also identify each buttons' functionality. One skilled in the art would appreciate that other shapes and markings can be used to identify the buttons without departing from the spirit and scope of the invention. For example, the markings can be recessed instead of raised.

In one embodiment, the indicator lights 825 may indicate that the VPU 20 is going through system start-up diagnostic testing when the one or more indicator lights 825 are blinking fast (more then once per second) and are green in color. The indicator lights 825 may indicate that the VPU 20 is operating normally when the one or more indicator lights 825 are blinking once per second and are green in color. The indicator lights 825 may indicate that the retinal stimulation system has a problem that was detected by the VPU 20 at start-up diagnostic when the one or more indicator lights 825 are blinking for example once per five second and are green in color. The indicator lights 825 may indicate that the video signal from camera 13 is not being received by the VPU 20 when the one or more indicator lights 825 are always on and are amber color. The indicator lights 825 may indicate that there is a loss of communication between the retinal stimulation system and the external coil 17 due to the movement or removal of Glasses 5 while the system is operational or if the VPU 20 detects a problem with the retinal stimulation system and shuts off power to the retinal stimulation system when the one or more indicator lights 825 are always on and are orange color. One skilled in the art would appreciate that other colors and blinking patterns can be used to give visual indication of operating status of the system without departing from the spirit and scope of the invention.

In one embodiment, a single short beep from the speaker (not shown) may be used to indicate that one of the buttons 825, 805 or 810 have been pressed. A single beep followed by two more beeps from the speaker (not shown) may be used to indicate that VPU 20 is turned off. Two beeps from the speaker (not shown) may be used to indicate that VPU 20 is starting up. Three beeps from the speaker (not shown) may be used to indicate that an error has occurred and the VPU 20 is about to shut down automatically. As would be clear to one skilled in the art, different periodic beeping may also be used to indicate a low battery voltage warning, that there is a problem with the video signal, and/or there is a loss of communication between the retinal stimulation system and the external coil 17. One skilled in the art would appreciate that other sounds can be used to give audio indication of operating status of the system without departing from the spirit and scope of the invention. For example, the beeps may be replaced by an actual prerecorded voice indicating operating status of the system.

In one exemplary embodiment, the VPU 20 is in constant communication with the retinal stimulation system through forward and backward telemetry. In this document, the forward telemetry refers to transmission from VPU 20 to the retinal stimulation system and the backward telemetry refers to transmissions from the Retinal stimulation system to the VPU 20. During the initial setup, the VPU 20 may transmit null frames (containing no stimulation information) until the VPU 20 synchronizes with the Retinal stimulation system via the back telemetry. In one embodiment, an audio alarm may be used to indicate whenever the synchronization has been lost.

In order to supply power and data to the Retinal stimulation system, the VPU 20 may drive the external coil 17, for example, with a 3 MHz signal. To protect the subject, the retinal stimulation system may comprise a failure detection circuit to detect direct current leakage and to notify the VPU 20 through back telemetry so that the visual prosthesis apparatus can be shut down.

The forward telemetry data (transmitted for example at 122.76 kHz) may be modulated onto the exemplary 3 MHz carrier using Amplitude Shift Keying (ASK), while the back telemetry data (transmitted for example at 3.8 kHz) may be modulated using Frequency Shift Keying (FSK) with, for example, 442 kHz and 457 kHz. The theoretical bit error rates can be calculated for both the ASK and FSK scheme assuming a ratio of signal to noise (SNR). The system disclosed in the present disclosure can be reasonably expected to see bit error rates of $10^{-5}$ on forward telemetry and $10^{-3}$ on back telemetry. These errors may be caught more than 99.998% of the time by both an ASIC hardware telemetry error detection algorithm and the VPU 20's firmware. For the forward telemetry, this is due to the fact that a 16-bit cyclic redundancy check (CRC) is calculated for every 1024 bits sent to the ASIC within electronics package 14 of the Retinal Stimulation System. The ASIC of the Retinal Stimulation System verifies this CRC and handles corrupt data by entering a non-stimulating 'safe' state and reporting that a telemetry error was detected to the VPU 20 via back telemetry. During the 'safe' mode, the VPU 20 may attempt to return the implant to an operating state. This recovery may be on the order of milliseconds. The back telemetry words are checked for a 16-bit header and a single parity bit. For further protection against corrupt data being misread, the back telemetry is only checked for header and parity if it is recognized as properly encoded Biphase Mark Encoded (BPM) data. If the VPU 20 detects invalid back telemetry data, the VPU 20 immediately changes mode to a 'safe' mode where the Retinal Stimulation System is reset and the VPU 20 only sends non-stimulating data frames.

Back telemetry errors cannot cause the VPU 20 to do anything that would be unsafe.

Figure 13A:
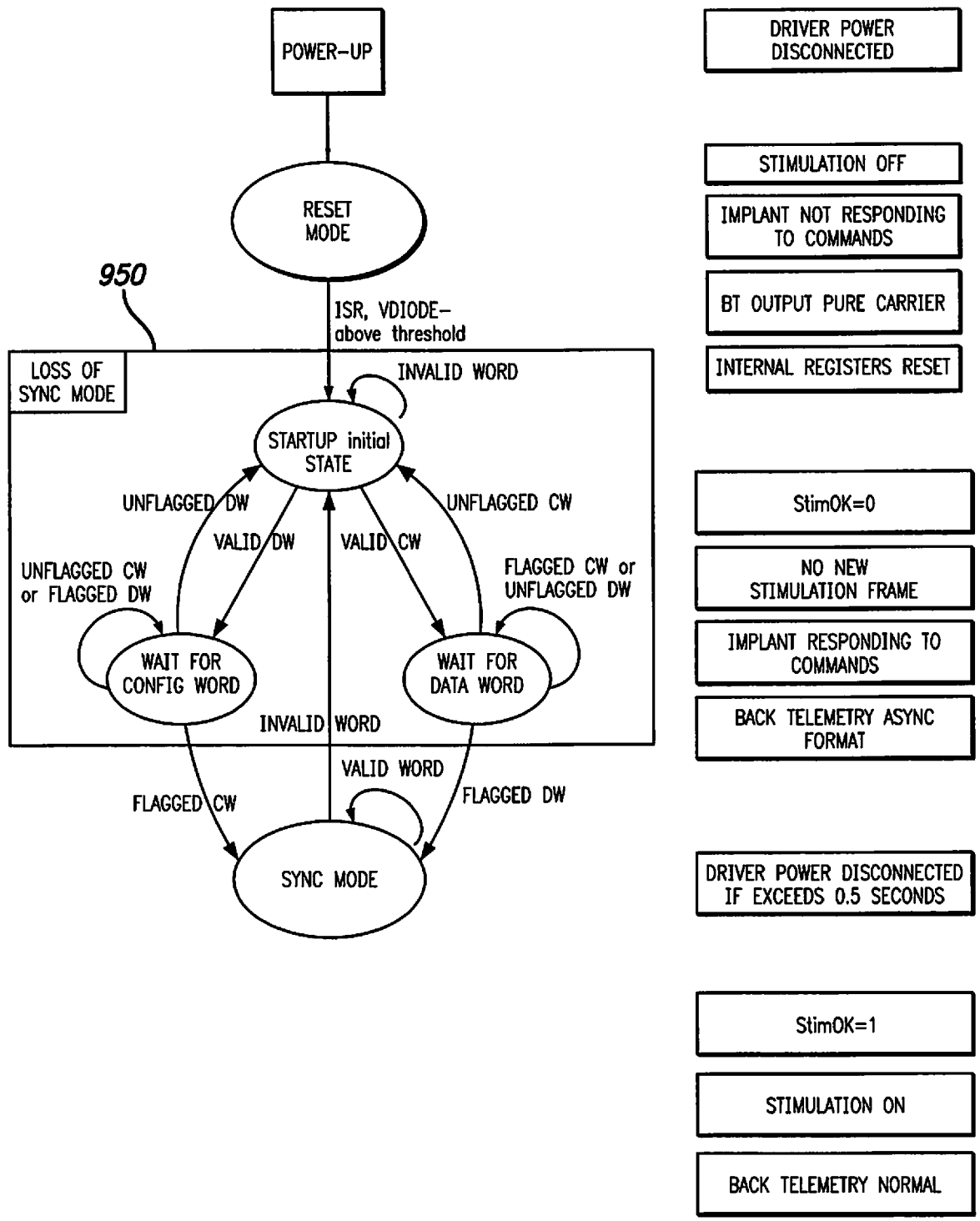
FIG. 13*a* shows a LOSS OF SYNC mode.

The response to errors detected in data transmitted by VPU 20 may begin at the ASIC of the Retinal Stimulation System. The Retinal Stimulation System may be constantly checking the headers and CRCs of incoming data frames. If either the header or CRC check fails, the ASIC of the Retinal Stimulation System may enter a mode called LOSS OF SYNC 950, shown in FIG. 13a. In LOSS OF SYNC mode 950, the Retinal Stimulation System will no longer produce a stimulation output, even if commanded to do so by the VPU 20. This cessation of stimulation occurs after the end of the stimulation frame in which the LOSS OF SYNC mode 950 is entered, thus avoiding the possibility of unbalanced pulses not completing stimulation. If the Retinal Stimulation System remains in a LOSS OF SYNC mode 950 for 1 second or more (for example, caused by successive errors in data transmitted by VPU 20), the ASIC of the Retinal Stimulation System disconnects the power lines to the stimulation pulse drivers. This eliminates the possibility of any leakage from the power supply in a prolonged LOSS OF SYNC mode 950. From the LOSS OF SYNC mode 950, the Retinal Stimulation System will not re-enter a stimulating mode until it has been properly initialized with valid data transmitted by the VPU 20.

In addition, the VPU 20 may also take action when notified of the LOSS OF SYNC mode 950. As soon as the Retinal Stimulation System enters the LOSS OF SYNC mode 950, the Retinal Stimulation System reports this fact to the VPU 20 through back telemetry. When the VPU 20 detects that the Retinal Stimulation System is in LOSS OF SYNC mode 950, the VPU 20 may start to send 'safe' data frames to the Retinal Stimulation System. 'Safe' data is data in which no stimulation output is programmed and the power to the stimulation drivers is also programmed to be off. The VPU 20 will not send data frames to the Retinal Stimulation System with stimulation commands until the VPU 20 first receives back telemetry from the Retinal Stimulation System indicating that the Retinal Stimulation System has exited the LOSS OF SYNC mode 950. After several unsuccessful retries by the VPU 20 to take the implant out of LOSS OF SYNC mode 950, the VPU 20 will enter a Low Power Mode (described below) in which the implant is only powered for a very short time. In this time, the VPU 20 checks the status of the implant. If the implant continues to report a LOSS OF SYNC mode 950, the VPU 20 turns power off to the Retinal Stimulation System and tries again later. Since there is no possibility of the implant electronics causing damage when it is not powered, this mode is considered very safe.

Due to an unwanted electromagnetic interference (EMI) or electrostatic discharge (ESD) event the VPU 20 data, specifically the VPU firmware code, in RAM can potentially get corrupted and may cause the VPU 20 firmware to freeze. As a result, the VPU 20 firmware will stop resetting the hardware watchdog circuit, which may cause the system to reset. This will cause the watchdog timer to expire causing a system reset in, for example, less than 2.25 seconds. Upon recovering from the reset, the VPU 20 firmware logs the event and shuts itself down. VPU 20 will not allow system usage after this occurs once. This prevents the VPU 20 code from freezing for extended periods of time and hence reduces the probability of the VPU sending invalid data frames to the implant.

Supplying power to the Retinal stimulation system can be a significant portion of the VPU 20's total power consumption. When the Retinal stimulation system is not within receiving range to receive either power or data from the VPU 20, the power used by the VPU 20 is wasted.

Power delivered to the Retinal stimulation system may be dependent on the orientation of the coils 17 and 16. The power delivered to the Retinal stimulation system may be controlled, for example, via the VPU 20 every 16.6 ms. The Retinal stimulation system may report how much power it receives and the VPU 20 may adjust the power supply voltage of the RF driver to maintain a required power level on the Retinal stimulation system. Two types of power loss may occur: 1) long term (>~1 second) and 2) short term (<~1 second). The long term power loss may be caused, for example, by a subject removing the Glasses 5.

Figure 13B:
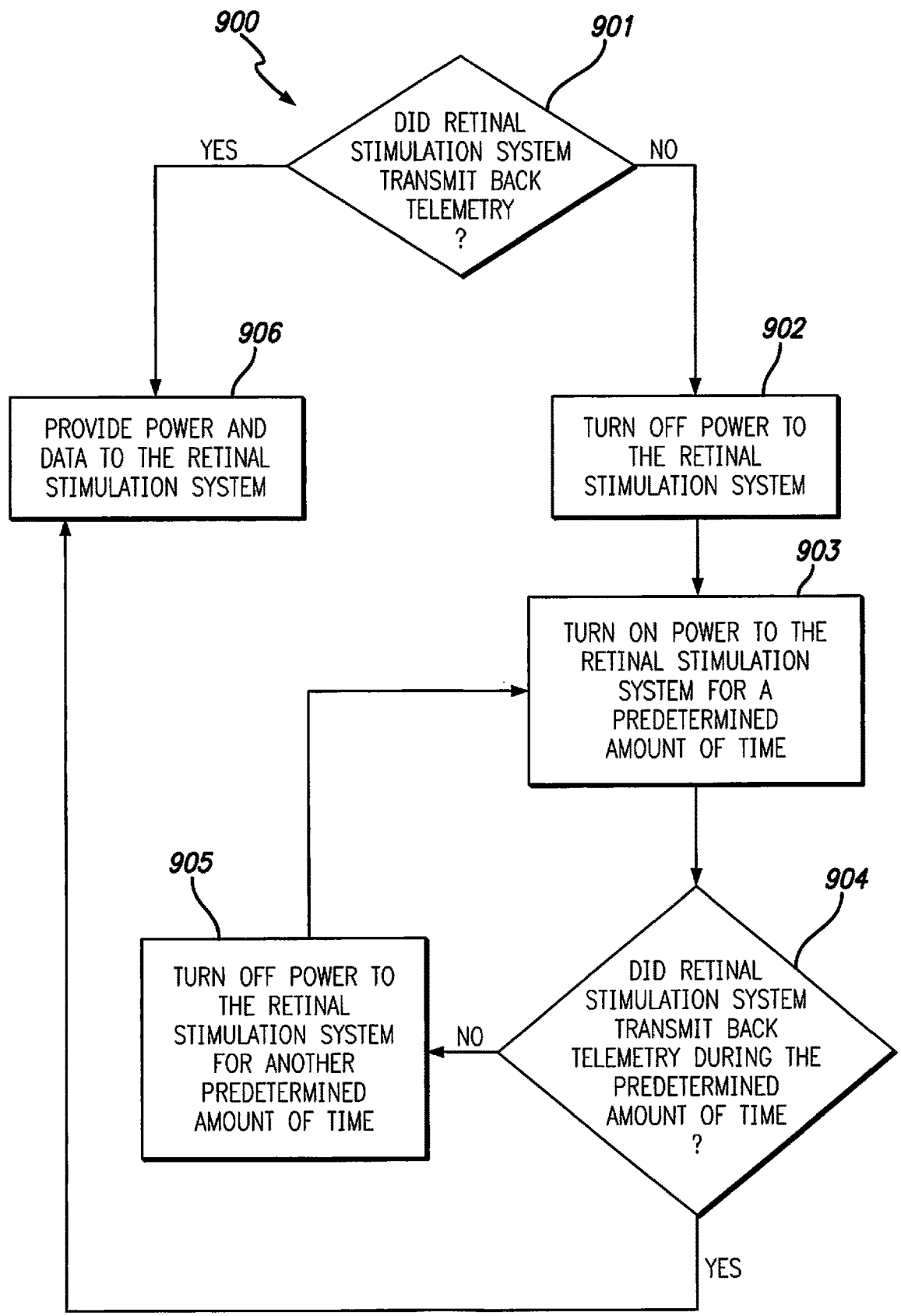
FIG. 13*b* shows an exemplary block diagram of the steps taken when VPU does not receive back telemetry from the Retinal stimulation system.

In one exemplary embodiment, the Low Power Mode may be implemented to save power for VPU 20. The Low Power Mode may be entered, for example, anytime the VPU 20 does not receive back telemetry from the Retinal stimulation system. Upon entry to the Low Power Mode, the VPU 20 turns off power to the Retinal stimulation system. After that, and periodically, the VPU 20 turns power back on to the Retinal stimulation system for an amount of time just long enough for the presence of the Retinal stimulation system to be recognized via its back telemetry. If the Retinal stimulation system is not immediately recognized, the controller again shuts off power to the Retinal stimulation system. In this way, the controller 'polls' for the passive Retinal stimulation system and a significant reduction in power used is seen when the Retinal stimulation system is too far away from its controller device. FIG. 13b depicts an exemplary block diagram 900 of the steps taken when the VPU 20 does not receive back telemetry from the Retinal stimulation system. If the VPU 20 receives back telemetry from the Retinal stimulation system (output "YES" of step 901), the Retinal stimulation system may be provided with power and data (step 906). If the VPU 20 does not receive back telemetry from the Retinal stimulation system (output "NO" of step 901), the power to the Retinal stimulation system may be turned off. After some amount of time, power to the Retinal stimulation system may be turned on again for enough time to determine if the Retinal stimulation system is again transmitting back telemetry (step 903). If the Retinal stimulation system is again transmitting back telemetry (step 904), the Retinal stimulation system is provided with power and data (step 906). If the Retinal stimulation system is not transmitting back telemetry (step 904), the power to the Retinal stimulation system may again be turned off for a predetermined amount of time (step 905) and the process may be repeated until the Retinal stimulation system is again transmitting back telemetry.

Figure 13C:
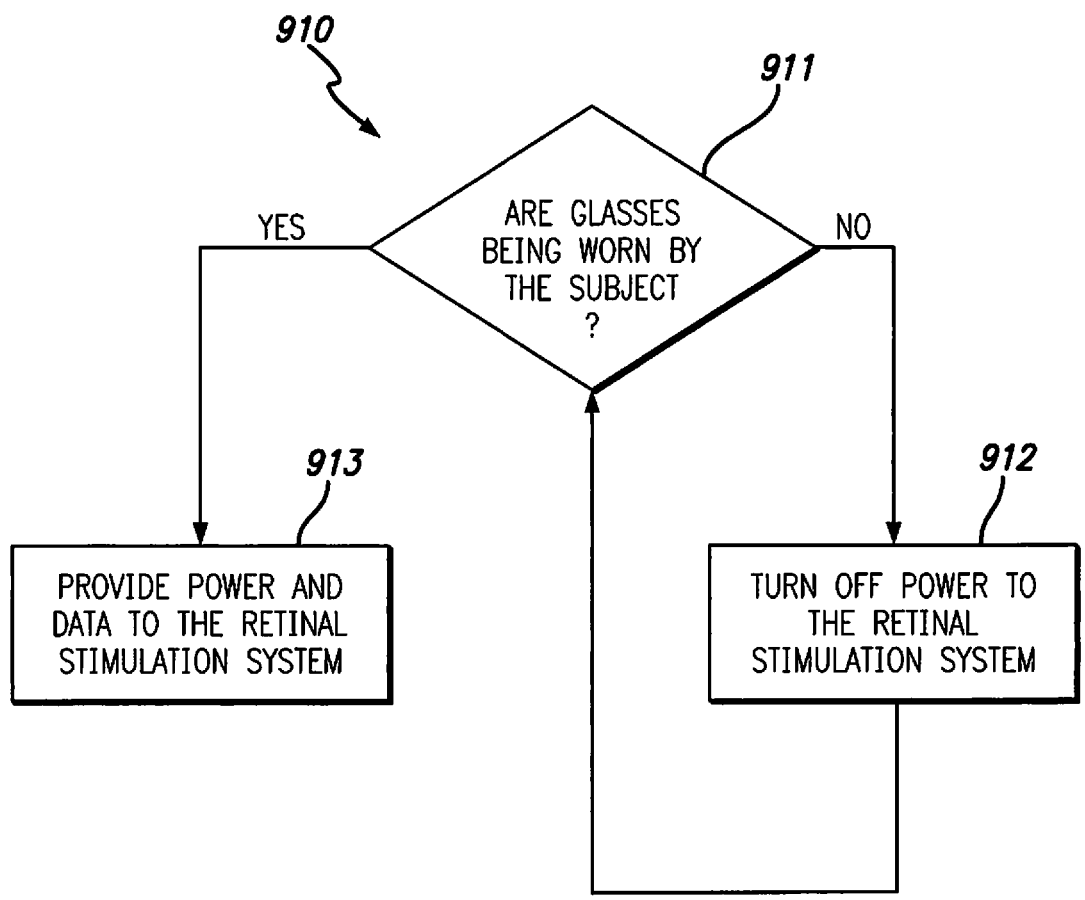
FIG. 13*c* shows an exemplary block diagram of the steps taken when the subject is not wearing Glasses.

In another exemplary embodiment, the Low Power Mode may be entered whenever the subject is not wearing the Glasses 5. In one example, the Glasses 5 may contain a capacitive touch sensor (not shown) to provide the VPU 20 digital information regarding whether or not the Glasses 5 are being worn by the subject. In this example, the Low Power Mode may be entered whenever the capacitive touch sensor detects that the subject is not wearing the Glasses 5. That is, if the subject removes the Glasses 5, the VPU 20 will shut off power to the external coil 17. As soon as the Glasses 5 are put back on, the VPU 20 will resume powering the external coil 17. FIG. 13c depicts an exemplary block diagram 910 of the steps taken when the capacitive touch sensor detects that the subject is not wearing the Glasses 5. If the subject is wearing Glasses 5 (step 911), the Retinal stimulation system is provided with power and data (step 913). If the subject is not wearing Glasses 5 (step 911), the power to the Retinal stimulation system is turned off (step 912) and the process is repeated until the subject is wearing Glasses 5.

Figures 1, 14:
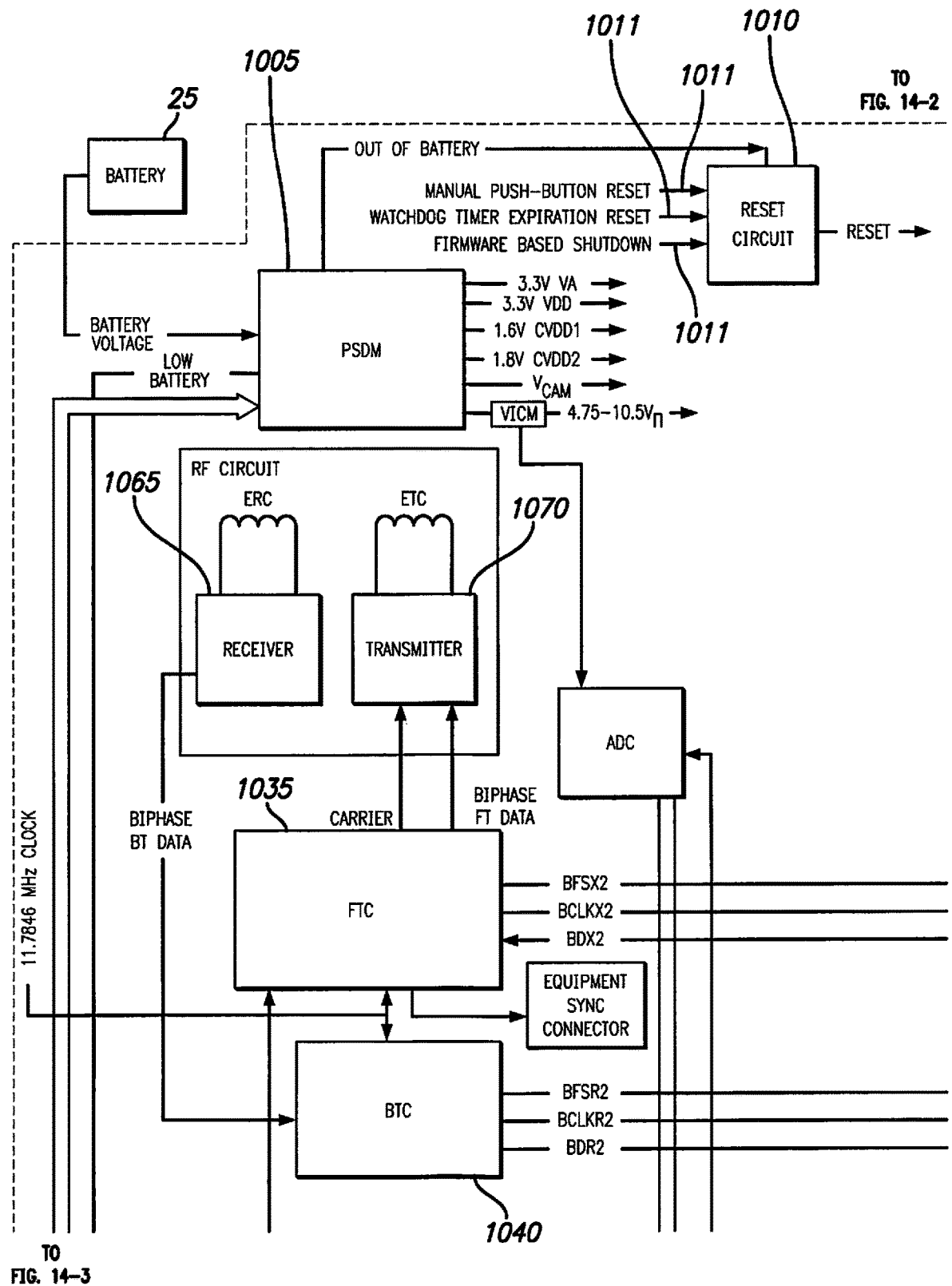
Figures 2, 14:
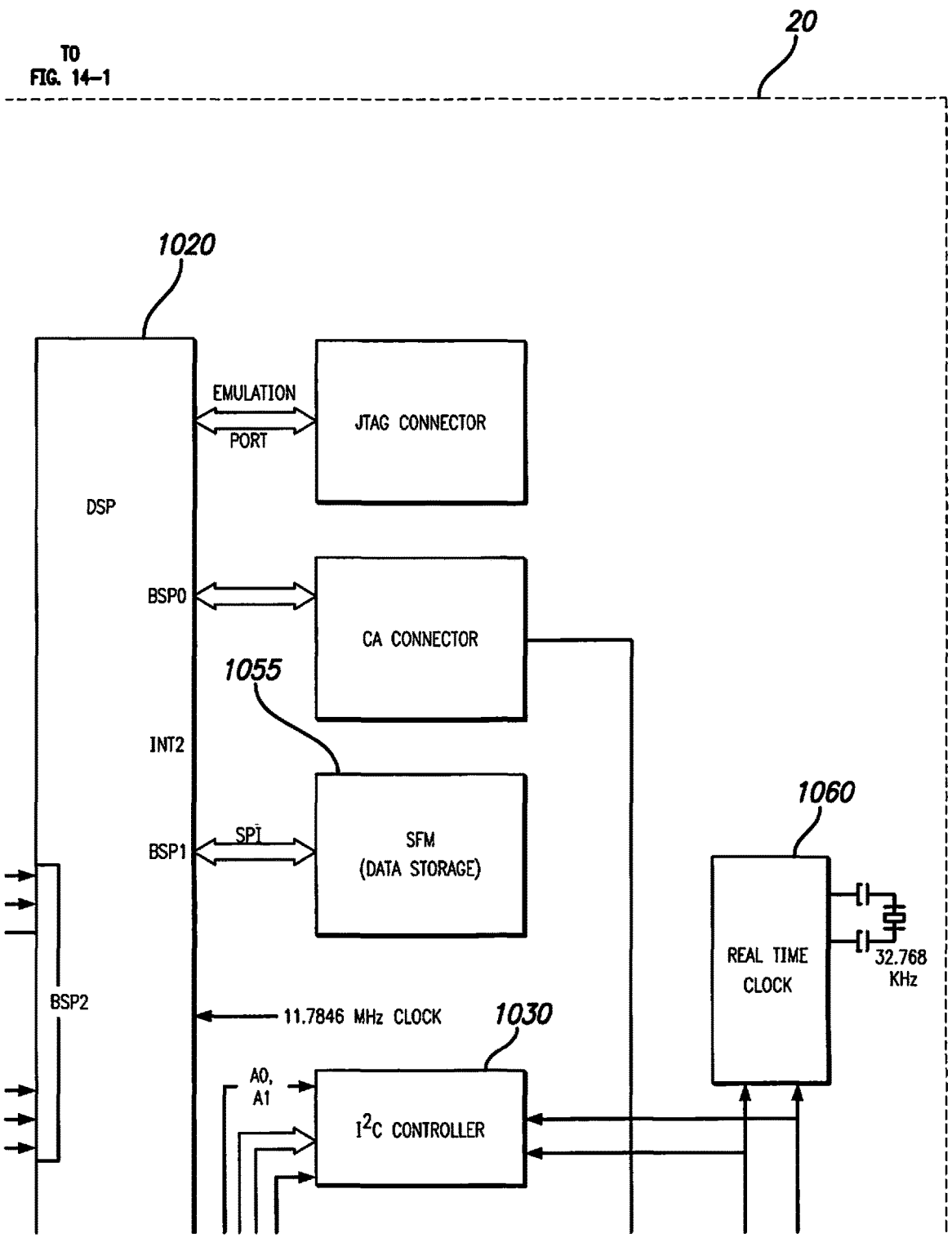
Figures 3, 14:
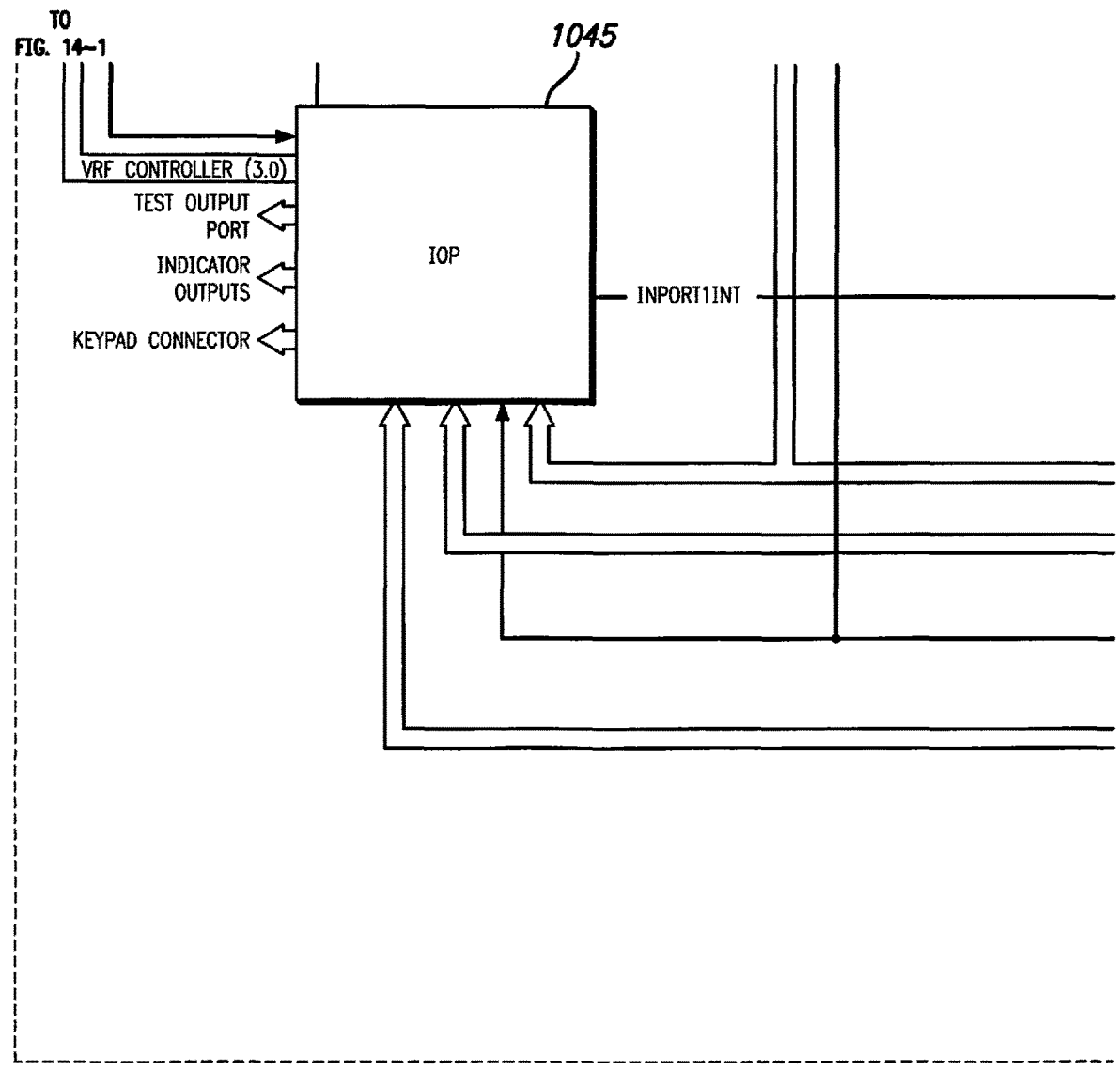
Figures 4, 14:
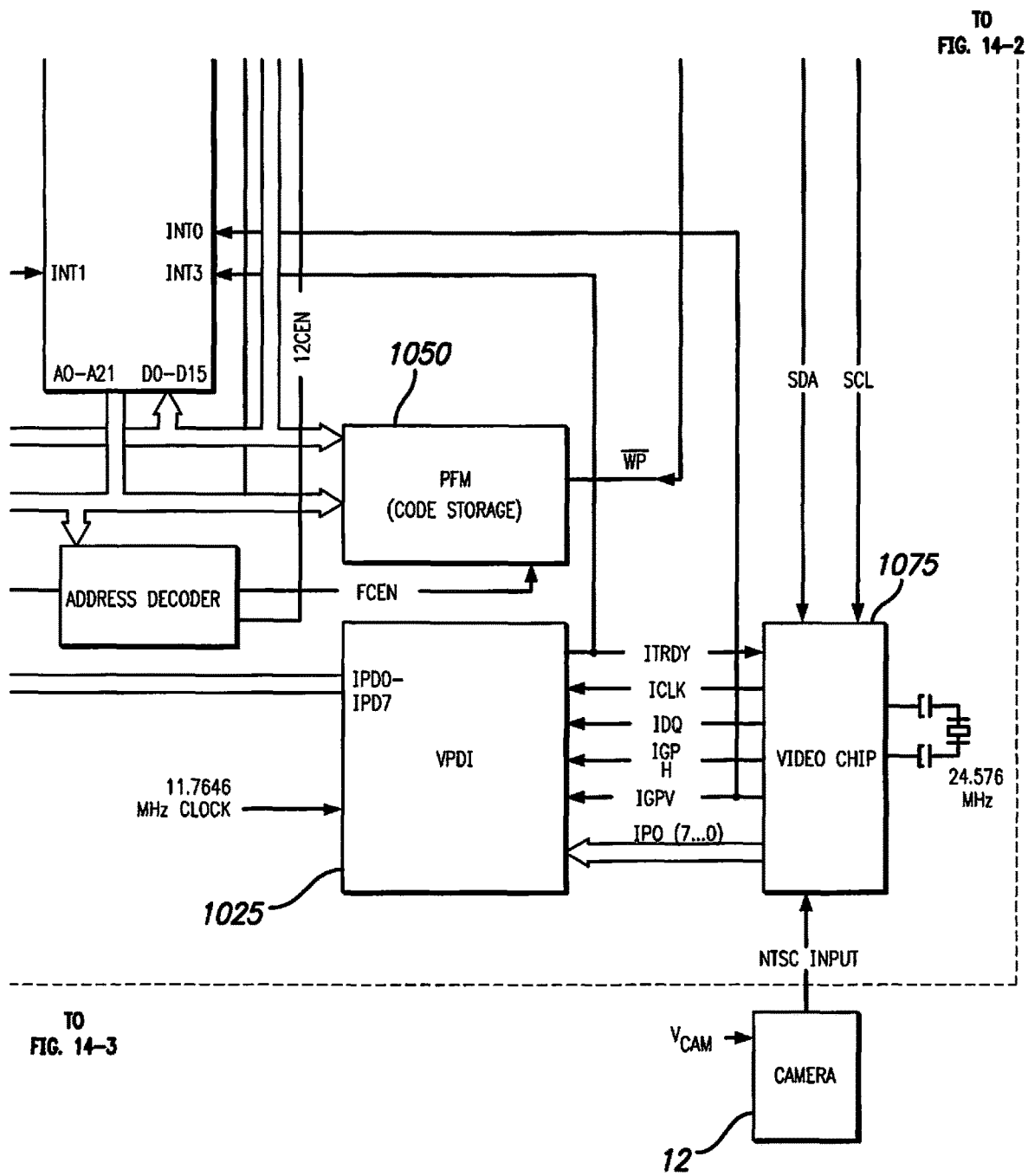

One exemplary embodiment of the VPU 20 is shown in FIG. 14. The VPU 20 may comprise: a Power Supply, a Distribution and Monitoring Circuit (PSDM) 1005, a Reset Circuit 1010, a System Main Clock (SMC) source (not shown), a Video Preprocessor Clock (VPC) source (not shown), a Digital Signal Processor (DSP) 1020, Video Preprocessor Data Interface 1025, a Video Preprocessor 1075, an PC Protocol Controller 1030, a Complex Programmable Logic device (CPLD) (not shown), a Forward Telemetry Controller (FTC) 1035, a Back Telemetry Controller (BTC) 1040, Input/Output Ports 1045, Memory Devices like a Parallel Flash Memory (PFM) 1050 and a Serial Flash Memory (SFM) 1055, a Real Time Clock 1060, an RF Voltage and Current Monitoring Circuit (VIMC) (not shown), a speaker and/or a buzzer, an RF receiver 1065, and an RF transmitter 1070.

The Power Supply, Distribution and Monitoring Circuit (PSDM) 1005 may regulate a variable battery voltage to several stable voltages that apply to components of the VPU 20. The Power Supply, Distribution and Monitoring Circuit (PSDM) 1005 may also provide low battery monitoring and depleted battery system cutoff. The Reset Circuit 1010 may have reset inputs 1011 that are able to invoke system level rest. For example, the reset inputs 1011 may be from a manual push-button reset, a watchdog timer expiration, and/or firmware based shutdown. The System Main Clock (SMC) source is a clock source for DSP 1020 and CPLD. The Video Preprocessor Clock (VPC) source is a clock source for the Video Processor. The DSP 1020 may act as the central processing unit of the VPU 20. The DSP 1020 may communicate with the rest of the components of the VPU 20 through parallel and serial interfaces. The Video Processor 1075 may convert the NTSC signal from the camera 13 into a down-scaled resolution digital image format. The Video Processor 1075 may comprise a video decoder (not shown) for converting the NTSC signal into high-resolution digitized image and a video scaler (not shown) for scaling down the high-resolution digitized image from the video decoder to an intermediate digitized image resolution. The video decoder may be composed of an Analog Input Processing, Chrominance and Luminance Processing and Brightness Contrast and Saturation (BSC) Control circuits. The video scaler may be composed of Acquisition control, Pre-scaler, BSC-control, Line Buffer and Output Interface. The I²C Protocol Controller 1030 may serve as a link between the DSP 1020 and the I²C bus. The I²C Protocol Controller 1030 may be able to convert the parallel bus interface of the DSP 1020 to the I²C protocol bus or vice versa. The I²C Protocol Controller 1030 may also be connected to the Video Processor 1075 and the Real Time Clock 1060. The VPDI 1025 may contain a tri-state machine to shift video data from Video Preprocessor 1075 to the DSP 1020. The Forward Telemetry Controller (FTC) 1035 packs 1024 bits of forward telemetry data into a forward telemetry frame. The FTC 1035 retrieves the forward telemetry data from the DSP 1020 and converts the data from logic level to biphase marked data. The Back Telemetry Controller (BTC) 1040 retrieves the biphase marked data from the RF receiver 1065, decodes it, and generates the BFSR, BCLKR and BDR for the DSP 1020. The Input/Output Ports 1045 provide expanded IO functions to access the CPLD on-chip and off-chip devices. The Parallel Flash Memory (PFM) 1050 may be used to store executable code and the Serial Flash Memory (SFM) 1055 may provide Serial Port Interface (SPI) for data storage. The VIMC may be used to sample and monitor RF transmitter 1070 current and voltage in order to monitor the integrity status of the retinal stimulation system.

Accordingly, what has been shown is an improved visual prosthesis and an improved method for limiting power consumption in a visual prosthesis. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A method of fitting an implantable neural stimulator comprising in order the steps of:
   a. providing an implantable neural stimulator including electrical components and an array of electrodes suitable to stimulate visual neurons;
   b. providing a computer, the computer completing steps c through 1 under automatic control of the computer;
   c. beginning recording electrically evoked response levels of measured neural activity;
   d. stimulating the visual neurons with a series of electrical stimulation signals through a selected subset of the array of electrodes;
   e. Stopping the recording electrically evoked response levels of measured neural activity;
   f. filtering the response signals;
   g. applying a wavelet transform to the response signals to filter out any artifacts caused by the electrical components in the implantable neural stimulator;
   h. discarding the response signals with large artifacts;
   i. averaging response signals measured during multiple epochs;
   j. comparing each level of the response signals to each level of the stimulation signals;
   k. determining a relationship between the each level of the stimulation signals and each level of the response signals;
   l. repeating steps c-k for different selected subsets of the array of electrodes;
   m. determining and storing desired levels of stimulation based upon the comparison of the levels of the response signals and the levels of the stimulation signals; and
   m. stimulating the visual neurons with the implantable neural stimulator to induce the perception of vision based on the desired levels of stimulation signals.

2. The method according to claim 1, wherein the step of stimulating the visual neurons includes increasing the electrical charge of the electrical stimulation signals until the neural activity is detected.

3. The method according to claim 1, wherein said step of stimulating the visual neurons includes decreasing the electrical stimulation signals when a predetermined level of the neural activity is reached.

4. The method according to claim 1, further comprising analysis of the delay period between the step of stimulating the visual neurons and the measurement of the neural activity, wherein the delay period varies according to a level of input stimulus, and this variation is used in the fitting process.

5. The method according to claim 1, wherein storing a level of stimulation includes storing a threshold for each electrode in the array of electrodes.

6. The method according to claim 1, further comprising ignoring the neural activity greater than a predetermined voltage.

7. The method according to claim 6, wherein the predetermined voltage is between 40 μV and 60 μV.

* * * * *